US010375325B2

(12) United States Patent
Schmidt

(10) Patent No.: US 10,375,325 B2
(45) Date of Patent: Aug. 6, 2019

(54) THERMAL ANOMALY DETECTION

(71) Applicant: Fluke Corporation, Everett, WA (US)

(72) Inventor: Matthew F. Schmidt, River Falls, WI (US)

(73) Assignee: Fluke Corporation, Everett, WA (US)

( * ) Notice: Subject to any disclaimer, the term of this patent is extended or adjusted under 35 U.S.C. 154(b) by 156 days.

(21) Appl. No.: 15/190,792

(22) Filed: Jun. 23, 2016

(65) Prior Publication Data

US 2017/0374296 A1 Dec. 28, 2017

(51) Int. Cl.
| | |
|---|---|
| *G01N 25/72* | (2006.01) |
| *G06K 9/62* | (2006.01) |
| *G06T 7/00* | (2017.01) |
| *G01J 5/02* | (2006.01) |
| *G01J 5/10* | (2006.01) |
| *H04N 5/33* | (2006.01) |
| *G01J 5/00* | (2006.01) |

(52) U.S. Cl.
CPC ............... *H04N 5/33* (2013.01); *G01J 5/025* (2013.01); *G01J 5/10* (2013.01); *G01N 25/72* (2013.01); *G06K 9/6212* (2013.01); *G06T 7/001* (2013.01); *G01J 2005/0077* (2013.01); *G06T 2207/10048* (2013.01)

(58) Field of Classification Search
CPC ......... H04N 5/33; G01N 25/72; G06K 9/6212
USPC ................................ 348/164, 125, 135–137
See application file for complete search history.

(56) References Cited

U.S. PATENT DOCUMENTS

| | | | |
|---|---|---|---|
| 7,535,002 B2 | 5/2009 | Johnson et al. | |
| 7,538,326 B2 | 5/2009 | Johnson et al. | |
| 7,924,312 B2 | 4/2011 | Packard | |
| 8,136,982 B2 | 3/2012 | Kumhyr et al. | |
| 8,286,112 B2 * | 10/2012 | Miranda | G06F 17/5031 716/110 |
| 8,374,438 B1 | 2/2013 | Wagner | |
| 8,498,836 B2 * | 7/2013 | Carlson | G01J 5/02 374/137 |
| 10,083,501 B2 * | 9/2018 | Stuart | G06T 7/0004 |
| 10,120,021 B1 * | 11/2018 | Silva | G01R 31/308 |

(Continued)

OTHER PUBLICATIONS

U.S. Appl. No. 14/837,757, filed Aug. 27, 2015, entitled Edge Enhancement for Thermal-Visible Combined Images and Cameras, 62 pages.

(Continued)

*Primary Examiner* — Paulos M Natnael
(74) *Attorney, Agent, or Firm* — Fredrikson & Byron, P.A.

(57) ABSTRACT

Systems and methods can be used to detect thermal anomalies in a target scene of an infrared image. Acquired thermal image data can be compared to a statistical thermal profile to detect thermal anomalies in the image data. Anomaly data based on the comparison can be used to generate an image representing locations and/or severity of detected anomalies. Systems can be used to acquire thermal image data for generating and/or updating statistical thermal profiles for use in anomaly detection processes. Auxiliary measurement devices can provide measurement data representative of one or more parameters of the target scene. The measurement data can be used to select from a plurality of possible statistical thermal profiles associated with the target scene to best match the current parameters of the scene.

27 Claims, 8 Drawing Sheets

(56) References Cited

U.S. PATENT DOCUMENTS

| | | | |
|---|---|---|---|
| 2002/0167987 A1* | 11/2002 | Schlagheck | G01N 25/72 374/5 |
| 2007/0198226 A1* | 8/2007 | Lee | G01W 1/17 702/189 |
| 2010/0036269 A1* | 2/2010 | Ferren | A61B 5/02007 600/504 |
| 2010/0131225 A1* | 5/2010 | Carlson | G01J 5/02 702/130 |
| 2010/0171825 A1* | 7/2010 | Cutsforth | G05B 23/0232 348/125 |
| 2013/0155249 A1* | 6/2013 | Neeley | H04N 5/33 348/159 |
| 2013/0162835 A1 | 6/2013 | Forland et al. | |
| 2013/0278771 A1 | 10/2013 | Magoun et al. | |
| 2015/0276491 A1 | 10/2015 | Rud | |
| 2015/0312489 A1* | 10/2015 | Hoelter | H04N 5/33 348/164 |
| 2016/0006951 A1* | 1/2016 | Moghadam | G03B 35/02 348/164 |
| 2016/0076937 A1 | 3/2016 | Stuart et al. | |
| 2016/0080666 A1 | 3/2016 | Stuart et al. | |
| 2016/0080667 A1 | 3/2016 | Stuart et al. | |
| 2016/0119592 A1 | 4/2016 | Stuart et al. | |
| 2016/0364629 A1* | 12/2016 | Solli | G06F 17/30268 |
| 2017/0116725 A1* | 4/2017 | Stuart | G06T 7/0004 |
| 2017/0140520 A1* | 5/2017 | Stuart | G06T 7/0004 |
| 2017/0374296 A1* | 12/2017 | Schmidt | G01J 5/025 |

OTHER PUBLICATIONS

European Pat. App. No. 17177689.1, Extended European Search Report dated Oct. 2, 2017, 11 pages.

* cited by examiner

THERMAL ANOMALY DETECTION

BACKGROUND

Thermal imaging cameras are used in a variety of situations. Thermal inspections of operating equipment can be used to quickly analyze the equipment without requiring invasive measurements or undesirable system downtime. However, interpreting thermal images usually requires substantial experience and specialized knowledge about the equipment being imaged in order to determine if the thermal imagery is showing "normal" or "abnormal" behavior.

Contributing to this difficulty is the fact that that indicated temperature readings from the imagery may not be sufficient, without further knowledge and/or information, to determine normal operation (i.e., equipment is operating properly) vs. abnormal operation (there's a problem). For example, a particular temperature reading (e.g. 75° C.) of a motor might be considered normal under certain load and ambient conditions, but under other conditions (lower load, lower ambient conditions, etc.), it could suggest a problem is present. Additionally or alternatively, thermal characteristics of certain portions of an object (e.g., a motor) may have greater fluctuations during use than other portions. An unfamiliar inspector may observe a hotter-than-usual location in an image and incorrectly assume abnormal operation.

SUMMARY

Aspects of the present disclosure are directed toward systems and methods for detecting thermal anomalies in a target scene. A thermal imaging device can be used to acquire thermal image data of a target scene. The acquired thermal image data can be compared to a statistical thermal profile representing typical thermal behavior of the target scene. Based on the comparison, anomaly data can be generated representing the degree of anomalousness of the received thermal image data with respect to the statistical thermal profile.

In some examples, the comparison is performed in a plurality of regions of the thermal image data and a corresponding plurality of regions in the statistical thermal profile. Anomaly data for each region can be generated for determining which, if any, regions in the target scene exhibit anomalous behavior. In various examples, detected anomalies can be indicated to a user, for example, via a graphical representation. Such graphical representations can visually indicate which regions in the thermal image data are the "most" anomalous.

Statistical thermal profiles can include a variety of statistical parameters, such as mean, median, standard deviation, percentile statistics, and the like. Such statistical parameters can be used to determine whether or not a region of thermal image data truly exhibits anomalous behavior. For instance, a region in the target scene having a regularly varying temperature may have a relatively large standard deviation in the corresponding statistical thermal profile. Thus, even if the acquired thermal image data shows a significant temperature change, such a condition may not be outside of the normal conditions, and may not be identified as anomalous.

In some examples, statistical thermal profiles can be associated with additional parameters of the target scene. Such additional parameters can impact the typical thermal profile of the target scene. For example, current draw of equipment in the target scene, ambient temperature, and/or other parameters can affect the overall thermal profile of the target scene. Thus, in some embodiments, one or more auxiliary test devices can be used to acquire additional parameters for selecting a statistical thermal profile associated with the current conditions of the target scene. The statistical thermal profile can be selected from a memory comprising a plurality of statistical thermal profiles based on determined parameters via an auxiliary test device in order to select the appropriate statistical thermal profile.

In some examples, thermal imaging devices can be used to acquire a plurality of infrared images in order to generate a statistical thermal profile. For example, when a device is operating in a known "normal" condition (e.g., a new or newly repaired device), acquired thermal images of the device are likely to represent non-anomalous thermal behavior. Such images can be used to generate a statistical thermal profile. In some examples, one or more auxiliary test devices can be used in attributing thermal image data to one or more statistical thermal profiles based on the condition of the target scene when the thermal image data is acquired.

DETAILED DESCRIPTION

The following detailed description is exemplary in nature and is not intended to limit the scope, applicability, or configuration of the invention in any way. Rather, the following description provides some practical illustrations for implementing various embodiments of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

A thermal imaging camera may be used to detect heat patterns across a scene, including an object or objects, under observation. The thermal imaging camera may detect infrared radiation given off by the scene and convert the infrared radiation into an infrared image indicative of the heat patterns. In some embodiments, the thermal imaging camera may also capture visible light from the scene and convert the visible light into a visible light image. Depending on the configuration of the thermal imaging camera, the camera may include infrared optics to focus the infrared radiation on an infrared sensor and visible light optics to focus the visible light on a visible light sensor.

Various embodiments provide methods and systems for producing thermal images with reduced noise using averaging techniques. To further improve image quality and eliminate problems that may arise from averaging (e.g. blurring, ghosting, etc.), an image alignment process is performed on the thermal images prior to averaging.

Figure 1:
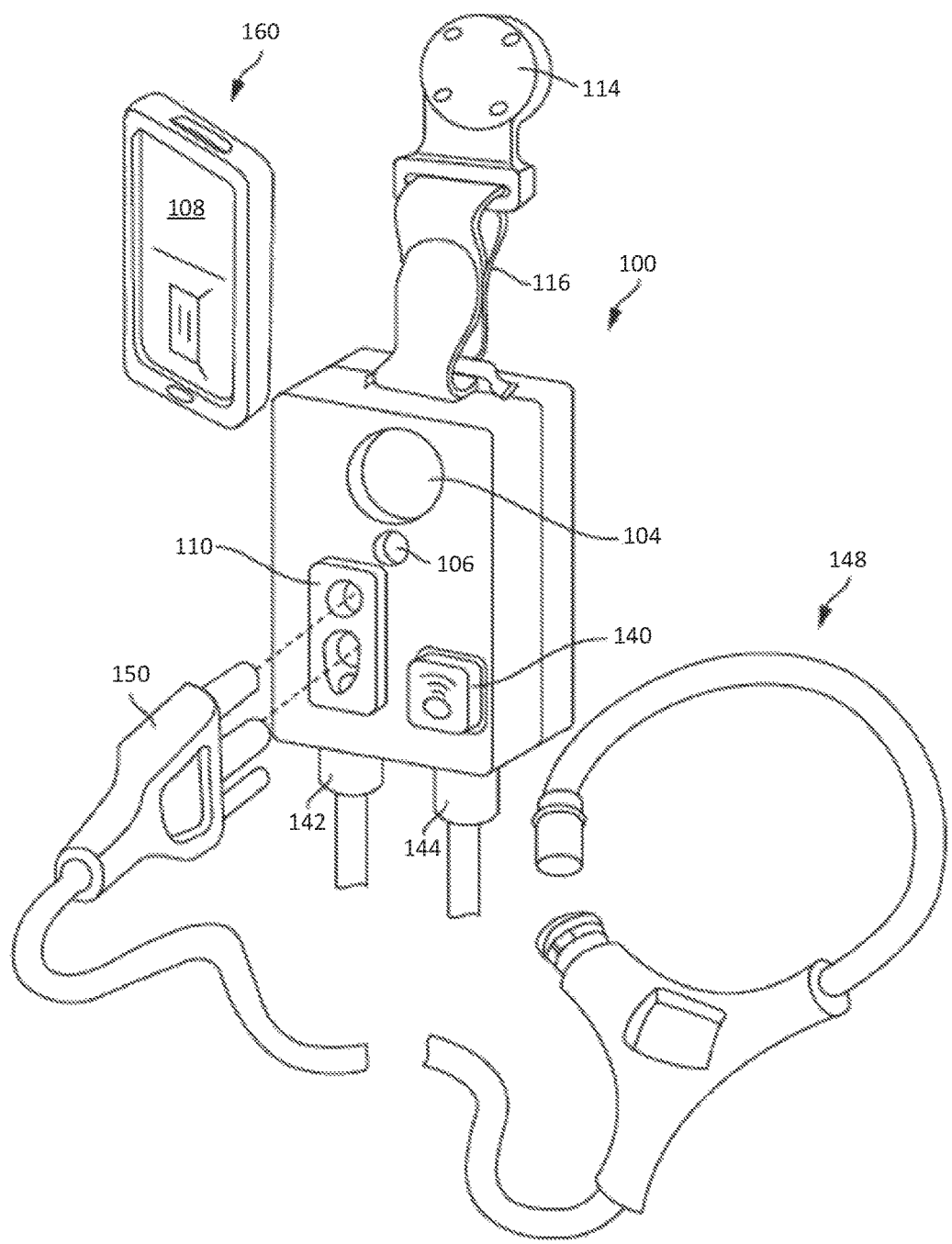
FIG. 1 shows a perspective view of an example thermal imaging camera.

FIG. 1 shows a perspective view of an example thermal imaging camera 100, which includes a housing 102, an infrared lens assembly 104, and a visible light lens assembly 106. Housing 102 houses the various components of thermal imaging camera 100. In the illustrated embodiment, the top portion of thermal imaging camera 100 includes an attachment mechanism 114 for permanently or removably affixing the camera 100 to a surface. In some instances, a user can affix the camera 100 to a surface or structure proximate equipment under test so that the equipment under test is in the field of view of the camera 100. The attachment mechanism 114 can include any appropriate material or construction for affixing to a surface or structure, such as a hook and loop material, a magnet, a snap, a clip, and the like. The attachment mechanism 114 can be secured to the camera 100 via a strap 116. In other embodiments, the attachment mechanism 114 can be attached directly to the camera 100.

Infrared lens assembly 104 receives infrared radiation from a scene and focuses the radiation on an infrared sensor for generating an infrared image of a scene. Visible light lens assembly 106 receives visible light from a scene and focuses the visible light on a visible light sensor for generating a visible light image of the same scene. Thermal imaging camera 100 captures the visible light image and/or the infrared image in response to a variety of possible prompts as described elsewhere herein.

Thermal imaging camera 100 may also include a focus mechanism (not shown) coupled to infrared lens assembly 104 that is configured to move at least one lens of the infrared lens assembly so as to adjust the focus of an infrared image generated by the thermal imaging camera. Additionally or alternatively, the focus mechanism may move the FPA relative to one or more lenses of the infrared lens assembly.

In operation, thermal imaging camera 100 detects heat patterns in a scene by receiving energy emitted in the infrared-wavelength spectrum from the scene and processing the infrared energy to generate a thermal image. Thermal imaging camera 100 may also generate a visible light image of the same scene by receiving energy in the visible light-wavelength spectrum and processing the visible light energy to generate a visible light image. As described in greater detail below, thermal imaging camera 100 may include an infrared camera module that is configured to capture an infrared image of the scene and a visible light camera module that is configured to capture a visible light image of the same scene. The infrared camera module may receive infrared radiation projected through infrared lens assembly 104 and generate therefrom infrared image data. The visible light camera module may receive light projected through visible light lens assembly 106 and generate therefrom visible light data.

In some examples, thermal imaging camera 100 collects or captures the infrared energy and visible light energy substantially simultaneously (e.g., at the same time) so that the visible light image and the infrared image generated by the camera are of the same scene at substantially the same time. In these examples, the infrared image generated by thermal imaging camera 100 is indicative of localized temperatures within the scene at a particular period of time while the visible light image generated by the camera is indicative of the same scene at the same period of time. In other examples, thermal imaging camera may capture infrared energy and visible light energy from a scene at different periods of time.

Visible light lens assembly 106 includes at least one lens that focuses visible light energy on a visible light sensor for generating a visible light image. Visible light lens assembly 106 defines a visible light optical axis which passes through the center of curvature of the at least one lens of the assembly. Visible light energy projects through a front of the lens and focuses on an opposite side of the lens. Visible light lens assembly 106 can include a single lens or a plurality of lenses (e.g., two, three, or more lenses) arranged in series. In addition, visible light lens assembly 106 can have a fixed focus or can include a focus adjustment mechanism for changing the focus of the visible light optics. In examples in which visible light lens assembly 106 includes a focus adjustment mechanism, the focus adjustment mechanism may be a manual adjustment mechanism or an automatic adjustment mechanism.

Infrared lens assembly 104 also includes at least one lens that focuses infrared energy on an infrared sensor for generating a thermal image. Infrared lens assembly 104 defines an infrared optical axis which passes through the center of curvature of lens of the assembly. During operation, infrared energy is directed through the front of the lens and focused on an opposite side of the lens. Infrared lens assembly 104 can include a single lens or a plurality of lenses (e.g., two, three, or more lenses), which may be arranged in series. In some examples, the infrared lens assembly 104 may include lenses having diffractive or reflective properties or elements. Additional optical components such as mirrors (e.g., Fresnel mirrors) and the like may be included within or otherwise proximate to the infrared lens assembly 104.

In some examples, thermal imaging camera 100 may include an automatically adjusting focus mechanism in addition to or in lieu of a manually adjusting focus mechanism. An automatically adjusting focus mechanism may be operatively coupled to at least one lens of infrared lens assembly 104 and configured to automatically move at least one lens to various focus positions, e.g., in response to instructions from thermal imaging camera 100. In one application of such an example, thermal imaging camera 100 may use a distance sensor such as a laser (not shown) to electronically measure a distance between an object in a target scene and the camera, referred to as the distance-to-target. Thermal imaging camera 100 may then control the automatically adjusting focus mechanism to move the at least one lens of infrared lens assembly 104 to a focus position that corresponds to the distance-to-target data determined by thermal imaging camera 100. The focus position may correspond to the distance-to-target data in that the focus position may be configured to place the object in the target scene at the determined distance in focus. In some examples, the focus position set by the automatically adjusting focus mechanism may be manually overridden by an operator, e.g., by interfacing with the camera.

During operation of thermal imaging camera 100, an operator may wish to view a thermal image of a scene and/or a visible light image of the same scene generated by the camera. For this reason, thermal imaging camera 100 may include or otherwise be in communication with a display. In the example of FIG. 1, thermal imaging camera 100 includes display 108 that is remote (e.g., separate) from infrared lens assembly 104 and visible light lens assembly 106 of thermal imaging camera 100, such as embedded in an external device 160.

Exemplary external devices (160) can include, for example, smartphones, tablets, computers, remote facilities, and the like. The external device 160 can generally communicate with the thermal imaging camera 100 via a wired or wireless communication. Wired connection can include USB, serial, or other known wired communication technology. Additionally or alternatively, wireless communication can include radio frequency (RF) communication, infrared (IR) communication, Wi-Fi, Zigbee, Bluetooth, or other known wireless communication technology. In some examples, the external device 160 can communicate with a thermal imaging camera 100 via a network (e.g., the Internet, a local area network, or other known communication networks) via wired communication, wireless communication, or a combination thereof.

Thermal imaging camera 100 can include a variety of user input media for controlling the operation of the camera and adjusting different settings of the camera. Example control functions may include adjusting the focus of the infrared and/or visible light optics, opening/closing a shutter, capturing an infrared and/or visible light image, or the like. In some examples, thermal imaging camera 100 includes interface elements such as a depressible trigger control and/or buttons for controlling other aspects of the operation of the camera. Different numbers or arrangements of user input media are possible, and it should be appreciated that the disclosure is not limited in this respect. For example, thermal imaging camera 100 may include a touch screen display which receives user input by depressing different portions of the screen.

In some embodiments, user input media can be integrated into an external device 160 in communication with the thermal imaging camera 100. In an exemplary embodiment, a smartphone or tablet (e.g., 160) having a touchscreen is in communication with a thermal imaging camera (e.g., 100). The touchscreen of the smartphone or tablet can provide a soft button interface for a user to interact with the thermal imaging camera, for example, via an application running on the external device.

In some examples, the camera includes an interface 110 capable of communicating with other equipment, such as with a measurement accessory 148 or other auxiliary measurement device. In the illustrated embodiment, camera 100 includes interface 110 for receiving an interfacing plug 150 of the measurement accessory 148. The camera 100 can receive a signal from the measurement accessory 148 via the interface 110 and generate measurement data therefrom. For example, in the illustrated embodiment, the auxiliary measurement accessory 148 can be configured to measure a parameter of equipment under test and/or the target scene, such as the current flowing through a conductor, the ambient temperature, or the measurement date, and communicate data to the camera 100 representative of measured parameter. Accordingly, camera 100 may include and/or function as an auxiliary measurement device generating measurement data representative of at least one parameter of a device under test. In some examples, the camera 100, the auxiliary measurement accessory 148 or the combination of the auxiliary measurement accessory 148 and the camera 100 may be referred to as test and measurement tools.

The camera 100 of FIG. 1 includes an IR imaging device (e.g., 104) and a VL imaging device (e.g., 106) for generating IR and VL image data representative of a target scene, respectively. IR and VL image data can be combined and displayed in any number of ways, such as those described in U.S. Pat. No. 7,535,002, entitled "CAMERA WITH VISIBLE LIGHT AND INFRARED BLENDING," which is assigned to the assignee of the instant application, and which is hereby incorporated by reference in its entirety. The IR and VL image data can be combined or otherwise displayed or analyzed by a user or a processing device. In some examples, the camera 100 includes a processor for performing any combination of processing IR and VL image data, processing measurement data from the measurement accessory 148, initiating one or more operations by one or more of the VL imaging device, the IR imaging device, and the measurement accessory 148 in response to received information, combining received data from any of such tools, or any other processing functions.

The illustrated system of FIG. 1 includes an external device 160, which can be in wired or wireless communication with the camera 100. The external device 160 can include a smartphone, tablet, or any other external device capable of performing any of receiving, processing, or displaying data. In some examples, the camera 100 includes a button 140 for activating a wireless interface of the camera 100. In some such examples, actuating button enables wireless communication between the camera 100 and an external device such as 160. In some embodiments, the button 140 can enable wireless communication between the camera 100 and an auxiliary measurement device, an external device 160, and/or a remote location, for example over a network. In some embodiments, wireless communication between the camera 100 and an external device 160 need not be initiated by button 140. For instance, in some examples, the camera 100 may be configured to communicate with any appropriate external device within communication range. In some examples, communication may be established automatically with an external device. In some such examples, communicating is established automatically with a device running appropriate software (e.g., a smartphone or tablet application). In still further embodiments, communication may be established from the external device.

The camera 100 of FIG. 1 includes a communication link 142 for communicating or receiving data or other signals to or from other devices. For instance, in some examples, the camera 100 can interface with the external device 160 or other equipment (e.g., an external auxiliary measurement device) via a wired connection to the communication link 142. In various embodiments, communication link 142 may provide for wired communication, wireless communication, or both.

The camera 100 can include a power input 144 for receiving power from a power source. For instance, the power input 144 can be coupled to an external power supply, such as a wall socket or other power supply. Additionally or alternatively, the camera 100 can include one or more batteries for powering the camera 100 or can parasitically receive power from a powered proximate device. In some examples, the power input 144 may provide electrical power to the imaging tool, an integrated auxiliary measurement device (e.g., via interface 110), or both.

In some examples, the camera 100 transmits data either wirelessly or via a wired connection (e.g., communication link 142) to a separate device, such as the external device 160 or other remote location. The separate device can analyze one or both of imaging data and measurement data, and can communicate commands back to the camera 100 in response to one or more satisfied thresholds or predetermined conditions. Additionally or alternatively, external device 160 can receive any combination of measurement data, IR image data, and VL image data from the camera 100. Accordingly, in some examples, the external device 160 can display any combination of such data, including measurement data (e.g., the amount of current flowing through a conductor), a VL image of the target scene, an IR image of the target scene, a combination VL and IR image of the target scene, and apparent temperature data of the target scene determined from the IR image data. In general, any combination of available data can be displayed.

While shown as directly interfacing with measurement accessory 148, thermal imaging camera 100 can be in wired or wireless communication with an auxiliary measurement device configured to generate measurement data. Additionally or alternatively, an external device (e.g., 160) can be in communication with both the thermal imaging camera 100 and an auxiliary measurement device and can perform some or all of the processing duties of received image and/or measurement data.

Figure 2:
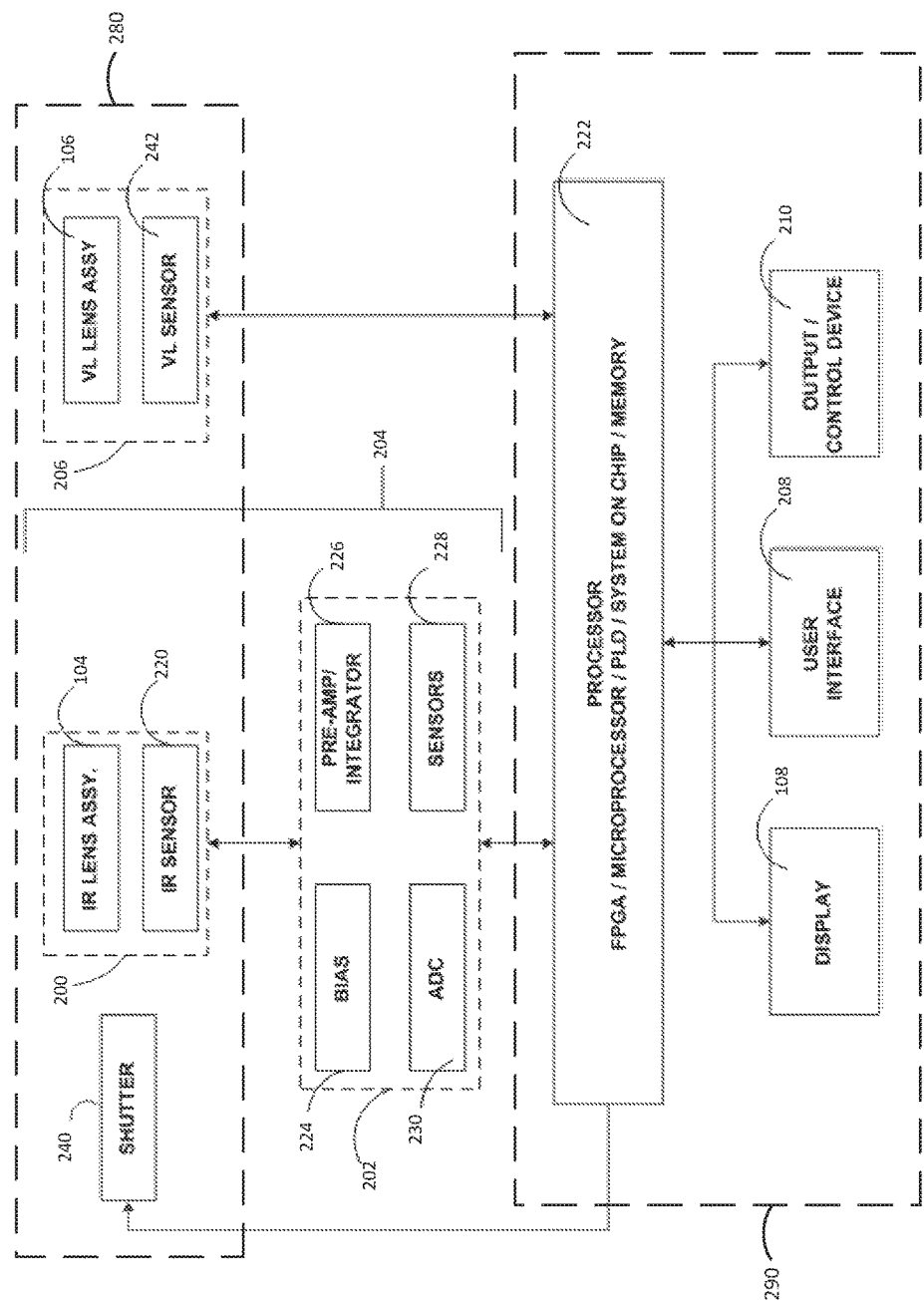
FIG. 2 is a functional block diagram illustrating components included in or in communication with an exemplary thermal imaging camera.

FIG. 2 is a functional block diagram illustrating components included in or in communication with an exemplary thermal imaging camera. Thermal imaging camera includes an IR camera module 200, front end circuitry 202. The IR camera module 200 and front end circuitry 202 are sometimes referred to in combination as front end stage or front end components 204 of the thermal imaging camera 100. Thermal imaging camera 100 may also include a visible light camera module 206, a display 108, a user interface 208, and an output/control device 210 (e.g., external device 160). As described elsewhere herein, some such components, such as a display 108 or a user interface 208, can be located separately from the thermal imaging camera (e.g., in external device 160).

Infrared camera module 200 may be configured to receive infrared energy emitted by a target scene and to focus the infrared energy on an infrared sensor for generation of infrared energy data, e.g., that can be displayed in the form of an infrared image on display 108 and/or stored in memory. Infrared camera module 200 can include any suitable components for performing the functions attributed to the module herein. In the example of FIG. 2, infrared camera module 200 is illustrated as including infrared lens assembly 104 and infrared sensor 220. As described above with respect to FIG. 1, infrared lens assembly 104 includes at least one lens that takes infrared energy emitted by a target scene and focuses the infrared energy on infrared sensor 220. Infrared sensor 220 responds to the focused infrared energy by generating an electrical signal that can be converted and displayed as an infrared image on display 108.

Infrared sensor 220 may include one or more focal plane arrays (FPA) that generate electrical signals in response to infrared energy received through infrared lens assembly 104. Each FPA can include a plurality of infrared sensor elements including, e.g., bolometers, photon detectors, or other suitable infrared sensor elements. In operation, each sensor element, which may each be referred to as a sensor pixel, may change an electrical characteristic (e.g., voltage or resistance) in response to absorbing infrared energy received from a target scene. In turn, the change in electrical characteristic can provide an electrical signal that can be received by a processor 222 and processed into an infrared image displayed on display 108.

For instance, in examples in which infrared sensor 220 includes a plurality of bolometers, each bolometer may absorb infrared energy focused through infrared lens assembly 104 and increase in temperature in response to the absorbed energy. The electrical resistance of each bolometer may change as the temperature of the bolometer changes.

With each detector element functioning as a sensor pixel, a two-dimensional image or picture representation of the infrared radiation can be further generated by translating the changes in resistance of each detector element into a time-multiplexed electrical signal that can be processed for visualization on a display or storage in memory (e.g., of a computer). Processor 222 may measure the change in resistance of each bolometer by applying a current (or voltage) to each bolometer and measure the resulting voltage (or current) across the bolometer. Based on these data, processor 222 can determine the amount of infrared energy emitted by different portions of a target scene and control display 108 to display a thermal image of the target scene.

Independent of the specific type of infrared sensor elements included in the FPA of infrared sensor 220, the FPA array can define any suitable size and shape. In some examples, infrared sensor 220 includes a plurality of infrared sensor elements arranged in a grid pattern such as, e.g., an array of sensor elements arranged in vertical columns and horizontal rows. In various examples, infrared sensor 220 may include an array of vertical columns by horizontal rows of, e.g., 16×16, 50×50, 160×120, 120×160, or 650×480. In other examples, infrared sensor 220 may include a smaller number of vertical columns and horizontal rows (e.g., 1×1), a larger number vertical columns and horizontal rows (e.g., 1000×1000), or a different ratio of columns to rows.

In certain embodiments a Read Out Integrated Circuit (ROIC) is incorporated on the IR sensor 220. The ROIC is used to output signals corresponding to each of the sensor pixels. Such ROIC is commonly fabricated as an integrated circuit on a silicon substrate. The plurality of detector elements may be fabricated on top of the ROIC, wherein their combination provides for the IR sensor 220. In some embodiments, the ROIC can include components discussed elsewhere in this disclosure (e.g. an analog-to-digital converter (ADC)) incorporated directly onto the FPA circuitry. Such integration of the ROIC, or other further levels of integration not explicitly discussed, should be considered within the scope of this disclosure.

As described above, the IR sensor 220 generates a series of electrical signals corresponding to the infrared radiation received by each infrared detector element to represent a thermal image. A "frame" of thermal image data is generated when the voltage signal from each infrared detector element is obtained by scanning all of the rows that make up the IR sensor 220. Again, in certain embodiments involving bolometers as the infrared detector elements, such scanning is done by switching a corresponding detector element into the system circuit and applying a bias voltage across such switched-in element. Successive frames of thermal image data are generated by repeatedly scanning the rows of the IR sensor 220, with such frames being produced at a rate sufficient to generate a video representation (e.g. 30 Hz, or 60 Hz) of the thermal image data.

The front end circuitry 202 includes circuitry for interfacing with and controlling the IR camera module 200. In addition, the front end circuitry 202 initially processes and transmits collected infrared image data to a processor 222 via a connection therebetween. More specifically, the signals generated by the IR sensor 220 are initially conditioned by the front end circuitry 202 of the thermal imaging camera 100. In certain embodiments, as shown, the front end circuitry 202 includes a bias generator 224 and a pre-amp/integrator 226. In addition to providing the detector bias, the bias generator 224 can optionally add or subtract an average bias current from the total current generated for each switched-in detector element. The average bias current can be changed in order (i) to compensate for deviations to the entire array of resistances of the detector elements resulting from changes in ambient temperatures inside the thermal imaging camera 100 and (ii) to compensate for array-to-array variations in the average detector elements of the IR sensor 220. Such bias compensation can be automatically controlled by the thermal imaging camera 100 or software, or can be user controlled via input to the output/control device 210 or processor 222. Following provision of the detector bias and optional subtraction or addition of the average bias current, the signals can be passed through a pre-amp/integrator 226. Typically, the pre-amp/integrator 226 is used to condition incoming signals, e.g., prior to their digitization. As a result, the incoming signals can be adjusted to a form that enables more effective interpretation of the signals, and in turn, can lead to more effective resolution of the created image. Subsequently, the conditioned signals are sent downstream into the processor 222 of the thermal imaging camera 100.

In some embodiments, the front end circuitry 202 can include one or more additional elements for example, an ADC 230 and/or one or more auxiliary measurement devices such as additional sensors or devices 228. Additional sensors 228 can include, for example, temperature sensors, visual light sensors (such as a CCD), pressure sensors, magnetic sensors, etc. Additionally or alternatively, auxiliary measurement devices can provide any variety of information, such as a time, date, or the like. Such sensors or other auxiliary measurement devices can provide additional calibration and detection information to enhance the functionality of the thermal imaging camera 100. For example, temperature sensors can provide an ambient temperature reading near the IR sensor 220 to assist in radiometry calculations. A magnetic sensor, such as a Hall Effect sensor, can be used in combination with a magnet mounted on the lens to provide lens focus position information. Such information can be useful for calculating distances, or determining a parallax offset for use with visual light scene data gathered from a visual light sensor.

An ADC 230 can provide the same function and operate in substantially the same manner as discussed below, however its inclusion in the front end circuitry 202 may provide certain benefits, for example, digitization of scene and other sensor information prior to transmittal to the processor 222 via the connection therebetween. In some embodiments, the ADC 230 can be integrated into the ROIC, as discussed above, thereby eliminating the need for a separately mounted and installed ADC 230.

In some embodiments, front end components can further include a shutter 240. A shutter 240 can be externally or internally located relative to the lens and operate to open or close the view provided by the infrared lens assembly 104. As is known in the art, the shutter 240 can be mechanically positionable, or can be actuated by an electro-mechanical device such as a DC motor or solenoid. Embodiments of the invention may include a calibration or setup software implemented method or setting which utilize the shutter 240 to establish appropriate bias levels for each detector element.

Components described as processors within thermal imaging camera 100, including processor 222, may be implemented as one or more processors, such as one or more microprocessors, digital signal processors (DSPs), application specific integrated circuits (ASICs), field programmable gate arrays (FPGAs), programmable logic circuitry, or the like, either alone or in any suitable combination. Processor 222 may also include memory that stores program instructions and related data that, when executed by processor 222, cause thermal imaging camera 100 and processor 222 to perform the functions attributed to them in this disclosure. Memory may include any fixed or removable magnetic, optical, or electrical media, such as RAM, ROM, CD-ROM, hard or floppy magnetic disks, EEPROM, or the like. Memory may also include a removable memory portion that may be used to provide memory updates or increases in memory capacities. A removable memory may also allow image data to be easily transferred to another computing device, or to be removed before thermal imaging camera 100 is used in another application. Processor 222 may also be implemented as a System on Chip that integrates some or all components of a computer or other electronic system into a single chip. These elements manipulate the conditioned scene image data delivered from the front end stages 204 in order to provide output scene data that can be displayed or stored for use by the user. Subsequently, the processor 222 (processing circuitry) sends the processed data to a display 108 or other output/control device 210.

During operation of thermal imaging camera 100, processor 222 can control infrared camera module 200 to generate infrared image data for creating an infrared image. Processor 222 can generate a digital "frame" of infrared image data. By generating a frame of infrared image data, processor 222 captures an infrared image of a target scene at substantially a given point in time. That is, in some examples, a plurality of pixels making up the infrared image may be captured simultaneously. In other embodiments, sets of one or more pixels may be captured serially until each pixel has been captured.

Processor 222 can capture a single infrared image or "snap shot" of a target scene by measuring the electrical signal of each infrared sensor element included in the FPA of infrared sensor 220 a single time. Alternatively, processor 222 can capture a plurality of infrared images of a target scene by repeatedly measuring the electrical signal of each infrared sensor element included in the FPA of infrared sensor 220. In examples in which processor 222 repeatedly measures the electrical signal of each infrared sensor element included in the FPA of infrared sensor 220, processor 222 may generate a dynamic thermal image (e.g., a video representation) of a target scene. For example, processor 222 may measure the electrical signal of each infrared sensor element included in the FPA at a rate sufficient to generate a video representation of thermal image data such as, e.g., 30 Hz or 60 Hz. Processor 222 may perform other operations in capturing an infrared image such as sequentially actuating a shutter 240 to open and close an aperture of infrared lens assembly 104, or the like.

With each sensor element of infrared sensor 220 functioning as a sensor pixel, processor 222 can generate a two-dimensional image or picture representation of the infrared radiation from a target scene by translating changes in an electrical characteristic (e.g., resistance) of each sensor element into a time-multiplexed electrical signal that can be processed, e.g., for visualization on display 108 and/or storage in memory. When displayed on a display 108, an infrared image can comprise a plurality of display pixels. Display pixels can have any defined relationship with corresponding sensor pixels. In some examples, each sensor pixel corresponds to a display pixel in an image representation of infrared data. In other examples, a plurality of sensor pixels may be combined (e.g., averaged) to provide infrared information for a single display pixel. In still other examples, a single sensor pixel may contribute to a plurality of display pixels. For example, a value from a single sensor pixel may be replicated at nearby pixels, such as in a simple upsampling procedure. In other examples, neighboring or otherwise nearby pixels may be averaged to create a new pixel value, such as in an interpolation procedure. Because relationships between display pixels and sensor pixels are defined with respect to camera operation, the generic term "pixel" may refer to the sensor pixel, the display pixel, or the data as it is processed from the sensor pixel to the display pixel unless otherwise stated. Processor 222 may perform computations to convert raw infrared image data into scene temperatures (radiometry) including, in some examples, colors corresponding to the scene temperatures.

Processor 222 may control display 108 to display at least a portion of an infrared image of a captured target scene. In some examples, processor 222 controls display 108 so that the electrical response of each sensor element of infrared sensor 220 is associated with a single pixel on display 108. In other examples, processor 222 may increase or decrease the resolution of an infrared image so that there are more or fewer pixels displayed on display 108 than there are sensor elements in infrared sensor 220. Processor 222 may control display 108 to display an entire infrared image (e.g., all portions of a target scene captured by thermal imaging camera 100) or less than an entire infrared image (e.g., a lesser port of the entire target scene captured by thermal imaging camera 100). Processor 222 may perform other image processing functions, as described in greater detail below.

Independent of the specific circuitry, thermal imaging camera 100 may be configured to manipulate data representative of a target scene so as to provide an output that can be displayed, stored, transmitted, or otherwise utilized by a user.

Thermal imaging camera 100 includes visible light camera module 206. Visible light camera modules are generally well known. For examples, various visible light camera modules are included in smartphones and numerous other devices. In some embodiments, visible light camera module 206 may be configured to receive visible light energy from a target scene and to focus the visible light energy on a visible light sensor for generation of visible light energy data, e.g., that can be displayed in the form of a visible light image on display 108 and/or stored in memory. Visible light camera module 206 can include any suitable components for performing the functions attributed to the module herein. In the example of FIG. 2, visible light camera module 206 is illustrated as including visible light lens assembly 106 and visible light sensor 242. As described above with respect to FIGS. 1 and 2, visible light lens assembly 106 includes at least one lens that takes visible light energy emitted by a target scene and focuses the visible light energy on visible light sensor 242. Visible light sensor 242 responds to the focused energy by generating an electrical signal that can be converted and displayed as a visible light image on display 108. In some examples, the visible light module 206 is configurable by a user, and can provide output, for example, to display 108, in a variety of formats. Visible light camera module 206 may include compensation functionality for varying lighting or other operating conditions or user preferences. The visible light camera module may provide a digital output including image data, which may include data in a variety of formats (e.g., RGB, CYMK, YCbCr, etc.).

Visible light sensor 242 may include a plurality of visible light sensor elements such as, e.g., CMOS detectors, CCD detectors, PIN diodes, avalanche photo diodes, or the like. The number of visible light sensor elements may be the same as or different than the number of infrared light sensor elements.

In operation, optical energy received from a target scene may pass through visible light lens assembly 106 and be focused on visible light sensor 242. When the optical energy impinges upon the visible light sensor elements of visible light sensor 242, photons within the photodetectors may be released and converted into a detection current. Processor 222 can process this detection current to form a visible light image of the target scene.

During use of thermal imaging camera 100, processor 222 can control visible light camera module 206 to generate visible light data from a captured target scene for creating a visible light image. The visible light data may include luminosity data indicative of the color(s) associated with different portions of the captured target scene and/or the magnitude of light associated with different portions of the captured target scene. Processor 222 can generate a "frame" of visible light image data by measuring the response of each visible light sensor element of thermal imaging camera 100 a single time. By generating a frame of visible light data, processor 222 captures visible light image of a target scene at a given point in time. Processor 222 may also repeatedly measure the response of each visible light sensor element of thermal imaging camera 100 so as to generate a dynamic thermal image (e.g., a video representation) of a target scene, as described above with respect to infrared camera module 200. In some examples, the visible light camera module 206 may include its own dedicated processor or other circuitry (e.g., ASIC) capable of operating the visible light camera module 206. In some such embodiments, the dedicated processor is in communication with processor 222 for providing visible light image data (e.g., RGB image data) to processor 222. In alternative embodiments, a dedicated processor for the visible light camera module 206 may be integrated into processor 222.

With each sensor element of visible light camera module 206 functioning as a sensor pixel, processor 222 can generate a two-dimensional image or picture representation of the visible light from a target scene by translating an electrical response of each sensor element into a time-multiplexed electrical signal that can be processed, e.g., for visualization on display 108 and/or storage in memory.

Processor 222 may control display 108 to display at least a portion of a visible light image of a captured target scene. In some examples, processor 222 controls display 108 so that the electrical response of each sensor element of visible light camera module 206 is associated with a single pixel on display 108. In other examples, processor 222 may increase or decrease the resolution of a visible light image so that there are more or fewer pixels displayed on display 108 than there are sensor elements in visible light camera module 206. Processor 222 may control display 108 to display an entire visible light image (e.g., all portions of a target scene captured by thermal imaging camera 100) or less than an entire visible light image (e.g., a lesser port of the entire target scene captured by thermal imaging camera 100).

In some embodiments, one or both of infrared 200 and visible light 206 camera modules for acquiring IR and VL image data may be included in an image acquisition module 280. The image acquisition module may be in wired or wireless communication with a processing module 290 that includes a processor such as 222. Processing module 290 may receive image data from the image acquisition module 280 and perform subsequent processing steps as will be described herein. In some examples, processing module 290 may include portable processing devices, such as a smartphone or a tablet. In some such embodiments, various components of front end circuitry 202 may be included in the image acquisition module 280, the processing module 290, or both.

In these and other examples, processor 222 may control display 108 to concurrently display at least a portion of the visible light image captured by thermal imaging camera 100 and at least a portion of the infrared image captured by thermal imaging camera 100. Such a concurrent display may be useful in that an operator may reference the features displayed in the visible light image to help understand the features concurrently displayed in the infrared image, as the operator may more easily recognize and distinguish different real-world features in the visible light image than the infrared image. In various examples, processor 222 may control display 108 to display the visible light image and the infrared image in side-by-side arrangement, in a picture-in-picture arrangement, where one of the images surrounds the other of the images, or any other suitable arrangement where the visible light and the infrared image are concurrently displayed.

For example, processor 222 may control display 108 to display the visible light image and the infrared image in a combined arrangement. In such an arrangement, for a pixel or set of pixels in the visible light image representative of a portion of the target scene, there exists a corresponding pixel or set of pixels in the infrared image, representative of substantially the same portion of the target scene. In various embodiments, the size and/or resolution of the IR and VL images need not be the same. Accordingly, there may exist a set of pixels in one of the IR or VL images that correspond to a single pixel in the other of the IR or VL image, or a set of pixels of a different size. Similarly, there may exist a pixel in one of the VL or IR images that corresponds to a set of pixels in the other image. Thus, as used herein, corresponding does not require a one-to-one pixel relationship, but may include mismatched sizes of pixels or groups of pixels. Various combination techniques of mismatched sized regions of images may be performed, such as up- or down-sampling one of the images, or combining a pixel with the average value of a corresponding set of pixels. Other examples are known and are within the scope of this disclosure.

Thus, corresponding pixels need not have a direct one-to-one relationship. Rather, in some embodiments, a single infrared pixel has a plurality of corresponding visible light pixels, or a visible light pixel has a plurality of corresponding infrared pixels. Additionally or alternatively, in some embodiments, not all visible light pixels have corresponding infrared pixels, or vice versa. Such embodiments may be indicative of, for example, a picture-in-picture type display as previously discussed. Thus, a visible light pixel will not necessarily have the same pixel coordinate within the visible light image as does a corresponding infrared pixel. Accordingly, as used herein, corresponding pixels generally refers pixels from any image (e.g., a visible light image, an infrared image, a combined image, a display image, etc.) comprising information from substantially the same portion of the target scene. Such pixels need not have a one-to-one relationship between images and need not have similar coordinate positions within their respective images.

Similarly, images having corresponding pixels (i.e., pixels representative of the same portion of the target scene) can be referred to as corresponding images. Thus, in some such arrangements, the corresponding visible light image and the infrared image may be superimposed on top of one another, at corresponding pixels. An operator may interact with user interface 208 to control the transparency or opaqueness of one or both of the images displayed on display 108. For example, the operator may interact with user interface 208 to adjust the infrared image between being completely transparent and completely opaque and also adjust the visible light image between being completely transparent and completely opaque. Such an exemplary combined arrangement, which may be referred to as an alpha-blended arrangement, may allow an operator to adjust display 108 to display an infrared-only image, a visible light-only image, of any overlapping combination of the two images between the extremes of an infrared-only image and a visible light-only image. Processor 222 may also combine scene information with other data, such as radiometric data, alarm data, and the like. In general, an alpha-blended combination of visible light and infrared images can comprise anywhere from 100 percent infrared and 0 percent visible light to 0 percent infrared and 100 percent visible light. In some embodiments, the amount of blending can be adjusted by a user of the camera. Thus, in some embodiments, a blended image can be adjusted between 100 percent visible light and 100 percent infrared.

Additionally, in some embodiments, the processor 222 can interpret and execute commands from user interface 208, and/or output/control device 210. This can involve processing of various input signals and transferring those signals to the front end circuitry 202 via a connection therebetween. Components (e.g. motors, or solenoids) proximate the front end circuitry 202 can be actuated to accomplish the desired control function. Exemplary control functions can include adjusting the focus, opening/closing a shutter, triggering sensor readings, adjusting bias values, etc. Moreover, input signals may be used to alter the processing of the image data that occurs in the processor 222.

Processor can further include other components to assist with the processing and control of the thermal imaging camera 100. For example, as discussed above, in some embodiments, an ADC can be incorporated into the processor 222. In such a case, analog signals conditioned by the front-end stages 204 are not digitized until reaching the processor 222. Moreover, some embodiments can include additional on board memory for storage of processing command information and scene data, prior to transmission to the display 108 or the output/control device 210.

An operator may interact with thermal imaging camera 100 via user interface 208, which may include buttons, keys, or another mechanism for receiving input from a user. The operator may receive output from thermal imaging camera 100 via display 108. Display 108 may be configured to display an infrared-image and/or a visible light image in any acceptable palette, or color scheme, and the palette may vary, e.g., in response to user control. In some examples, display 108 is configured to display an infrared image in a monochromatic palette such as grayscale. In other examples, display 108 is configured to display an infrared image in a color palette such as, e.g., amber, ironbow, blue-red, or other high contrast color scheme. Combinations of grayscale and color palette displays are also contemplated. In some examples, the display being configured to display such information may include processing capabilities for generating and presenting such image data. In other examples, being configured to display such information may include the ability to receive image data from other components, such as processor 222. For example, processor 222 may generate values (e.g., RGB values, grayscale values, or other display options) for each pixel to be displayed. Display 108 may receive such information and map each pixel into a visual display.

While processor 222 can control display 108 to concurrently display at least a portion of an infrared image and at least a portion of a visible light image in any suitable arrangement, a picture-in-picture arrangement may help an operator to easily focus and/or interpret a thermal image by displaying a corresponding visible image of the same scene in adjacent alignment.

A power supply (not shown) delivers operating power to the various components of thermal imaging camera 100 and, in some examples, may include a rechargeable or non-rechargeable battery and a power generation circuit.

During operation of thermal imaging camera 100, processor 222 controls infrared camera module 200 and visible light camera module 206 with the aid of instructions associated with program information that is stored in memory to generate a visible light image and an infrared image of a target scene. Processor 222 further controls display 108 to display the visible light image and/or the infrared image generated by thermal imaging camera 100.

Thermal imaging cameras can be employed in various systems and configurations to perform monitoring and/or analysis functions. For example, in some instances, a thermal imaging camera can be used to characterize operation of a piece of equipment under test based on the heat pattern of the equipment. Portions of the equipment operating at a temperature that is too high or too low can be an indication of equipment malfunction or other undesirable operating conditions. Observing the thermal profile of the equipment can be useful in identifying and addressing such issues.

In some cases, equipment under test is easily accessible by a technician who can manually perform thermal analysis of the equipment in order to observe any trends or anomalies in the heat pattern of the equipment. However, in other cases, equipment can be difficult to access, making manual inspection more cumbersome. Additionally or alternatively, a system or facility having many pieces of equipment can make an inspection process of each piece of equipment difficult and/or time intensive. Moreover, some facilities are not staffed with a trained technician such as a thermographer capable of performing thermal image analysis.

Aspects of this disclosure are generally directed toward systems and methods for providing enhanced thermal analysis for a target scene. In some embodiments, one or more thermal imaging cameras can be deployed proximate each piece of equipment for which thermal analysis is desired. In some such examples, such thermal imaging cameras can communicate with external devices such as smartphones, tablets, computers, remote monitoring facilities, and the like to facilitate observation of the thermal profile of the equipment. Some such systems are described in U.S. patent application Ser. No. 14/921,128, filed Oct. 23, 2015, and Ser. No. 14/855,989, filed Sep. 16, 2015, each of which is assigned to the assignee of the instant application and is hereby incorporated by reference in its entirety. In such arrangements, a thermal imaging camera can remain in the same position for continuous or periodic monitoring of a piece of equipment from substantially the same point of view.

Additionally or alternatively, in some embodiments, the camera can include or otherwise be in communication with one or more auxiliary measurement devices configured to acquire data representative of one or more parameters of the target scene and/or the equipment under test. Auxiliary measurement devices can include any of a variety of devices, such as test and measurement tools described in U.S. patent application Ser. No. 14/855,884, filed Sep. 16, 2015, which is assigned to the assignee of the instant application and is hereby incorporated by reference in its entirety. Exemplary auxiliary measurement devices can include, but are not limited to, digital multimeters, current measurement tools, power quality tools, vibration tools, portable oscilloscope tools, laser alignment tools, ultrasonic test tools, insulation resistance testers, multi-function electrical test tools, single-function electrical test tools, contact temperature measurement tools, humidity measurement tools, air-flow measurement tools, air temperature measurement tools, air quality and particulate measurement tools, clocks, calendars, or other devices capable of providing information representative of aspects of the target scene. The thermal imaging camera and the auxiliary measurement device(s) can be used individually and/or together to analyze behavior of the equipment under test.

In some such examples, the thermal imaging camera can be in wired or wireless communication with the auxiliary measurement device and/or an external device as described elsewhere herein. Similarly, the auxiliary measurement device can be in wired or wireless communication with the thermal imaging camera and/or an external device. In some examples, the thermal imaging camera and the auxiliary measurement device are in communication with one another as well as at least one common external device. In some such examples, one of the auxiliary measurement device and the thermal imaging camera can be in communication with the external device via the other of the auxiliary measurement device and the thermal imaging camera.

Figure 3:
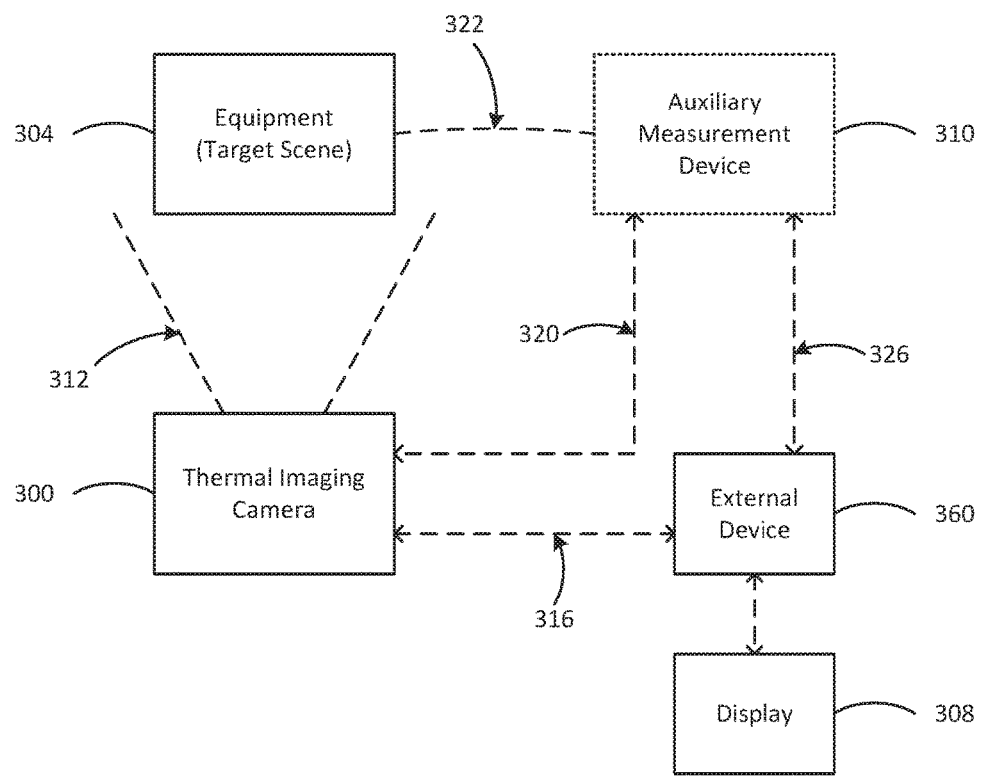
FIG. 3 is a schematic diagram illustrating an exemplary system for analyzing a target scene with respect to a statistical thermal profile.

FIG. 3 is a schematic diagram illustrating an exemplary system for analyzing equipment under test with respect to a statistical thermal profile. In the illustrated example, thermal imaging camera 300 is positioned proximate equipment under test 304 such that the equipment 304 is in the field of view 312 of the thermal imaging camera 300. The thermal imaging camera 300 can be configured to generate image data representative of the equipment 304. In an exemplary embodiment, thermal imaging camera 300 includes an infrared sensor array and is configured to generate infrared image data representative of the heat pattern of equipment 304. As described elsewhere herein, in some embodiments, the thermal imaging camera 300 further comprises a visible light camera module capable of detecting visible light radiation from the target scene (e.g., equipment 304) and generating visible light image data representative thereof. In some such embodiments, the visible light camera module is positioned proximate the infrared sensor array so that the visible light image data and infrared image data are representative of substantially the same scene. Thus, it will be appreciated that, as used herein, the term "thermal imaging camera" can be used to describe a device that, in addition to generating thermal image data, includes a visible light camera module and associated visible light imaging optics for acquiring visible light image data.

In the exemplary system, an auxiliary measurement device 310 is configured to measure one or more parameters of equipment 304 via connection 322. Connection 322 may be a wired or wireless connection. The auxiliary measurement device 310 is configured to generate measurement data representative of the at least one parameter of the equipment 304. In an exemplary embodiment, auxiliary measurement device 310 can include a DMM configured to measure the current flowing through the equipment 304 via a wired connection 322.

As shown, thermal imaging camera 300 can communicate with auxiliary measurement device 310 via communication link 320. Communication link 320 may include one- or two-way communication between thermal imaging camera 300 and auxiliary measurement device 310. In some examples, thermal imaging camera 300 may communicate image data to auxiliary measurement device 310 via communication link 320. Additionally or alternatively, auxiliary measurement device 310 can communicate measurement data to the thermal imaging camera 300 via communication link 320. One or both of auxiliary measurement device 310 and thermal imaging camera 300 can be configured to display one or both of the measurement data and the image data associated with equipment 304. In some embodiments, in addition to image data and/or measurement data, communication between the auxiliary measurement device 310 and the thermal imaging camera 300 can include command/control signals or other processing signals.

As shown in the illustrated embodiment, an external device 360 can communicate with one or both of thermal imaging camera 300 and auxiliary measurement device. In some embodiments, external device 360 can be capable of processing and/or displaying one or both of image data from the thermal imaging camera 300 and measurement data from auxiliary measurement device 310. In some examples, the external device 360 can be capable of acquiring image data from thermal imaging camera 300 via wired or wireless communication link 316 and measurement data from auxiliary measurement device 310 via wired or wireless communication link 326.

In some examples, the external device 360 includes or is otherwise in communication with a display 308 for presenting information regarding one or both of image data and measurement data. In some such embodiments, the external device 360 can combine measurement data and image data for presentation on a display 308. In some examples, display 308 is built-in to the external device 360, such as a smartphone, tablet, laptop computer, etc. In other examples, the display 308 may be built-in to one of the thermal imaging camera 300 and the auxiliary measurement device 310. Various such configurations are described in U.S. patent application Ser. No. 14/855,884, which is incorporated by reference.

In some examples, the thermal imaging camera 300 can include a fastener for temporary or permanent affixing to a location. Exemplary fasteners can include, for example, a magnet or a strap. Accordingly, in some examples, the thermal imaging camera 300 can be affixed proximate a piece of equipment under test or to be tested (e.g., equipment 304) in order to acquire image data regarding the equipment from the imaging tool. The imaging tool can be configured to function independently, in conjunction with, or physically connected to the auxiliary measurement device 310. In some examples, the thermal imaging camera 300 also can function in conjunction with, or be controlled by another external device 360.

In general, systems such as shown in FIG. 3 may include any number of imaging tools and/or auxiliary measurement devices. For example, a plurality of imaging tools may be used to acquire image data of an object under test from multiple perspectives or using multiple imaging techniques. Additionally or alternatively, a plurality of auxiliary measurement devices may be used to determine a plurality of parameters of the object under test. Image data and measurement data from any number of imaging tools and auxiliary measurement devices may be communicated to a central location (e.g., a single imaging tool, auxiliary measurement device, external device, etc.) for performing any of processing, combining, and displaying the acquired data.

Figure 4:
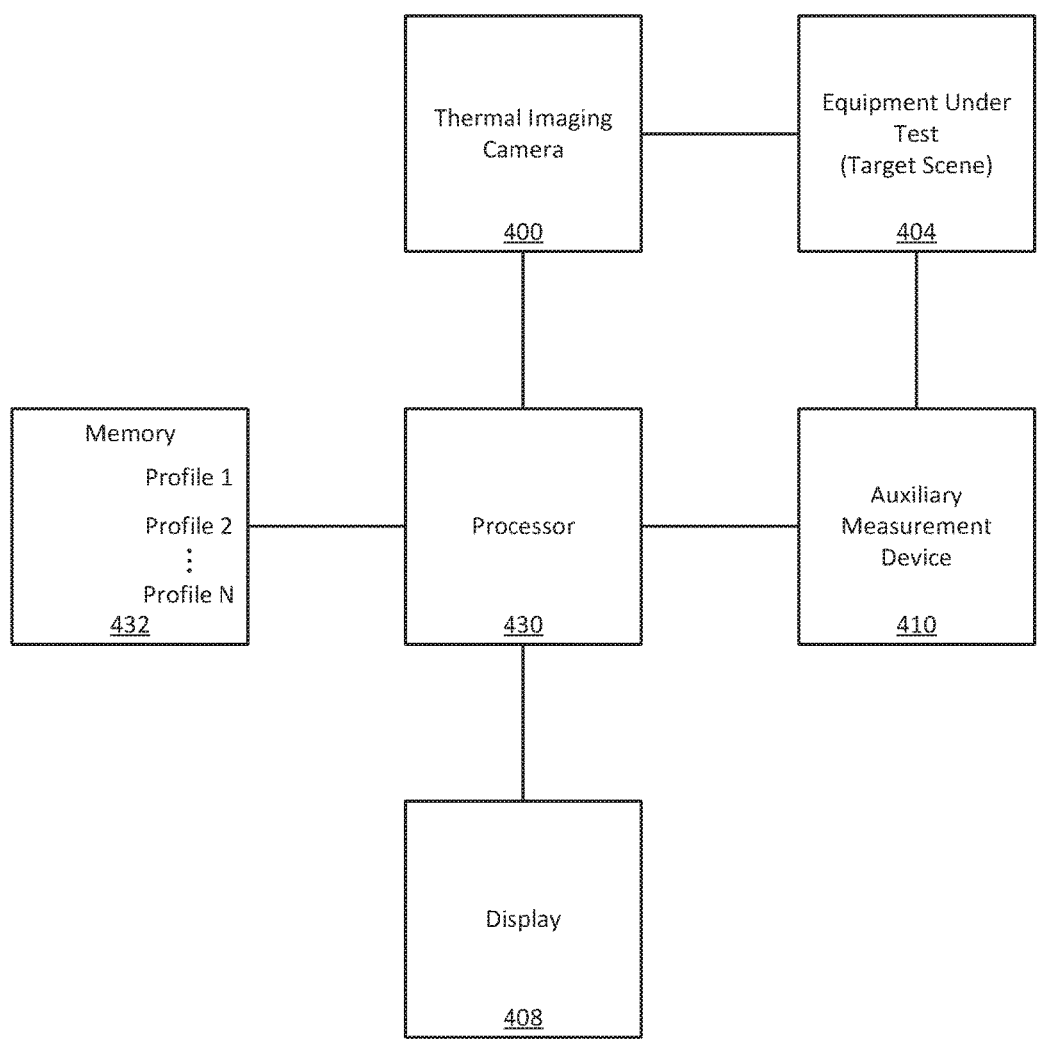
FIG. 4 is a schematic block diagram showing communication between system components according to some embodiments.

FIG. 4 is a schematic block diagram showing communication between system components according to some embodiments. In the illustrated example, thermal imaging camera 400 is configured to generate thermal image data representative of equipment under test 404. Similarly, auxiliary measurement device 410 is configured to generate measurement data representative of at least one parameter of the equipment under test 404.

The thermal imaging camera 400 and auxiliary measurement device 410 are in communication with a processor 430. The processor 430 can be capable of receiving signals from one or both of the thermal imaging camera 400 and the auxiliary measurement device 410. In some examples, the processor 430 can be a part of the thermal imaging camera 400 or the auxiliary measurement device 410. In other examples, the processor can be included in a separate component, such as an external device (e.g., 360 of FIG. 3). In some embodiments, functioning of processor 430 as herein described can be divided between multiple physical components, such as a processor within any one or more of the thermal imaging camera 400, the auxiliary measurement device 410, or an external device (e.g., 360).

In some configurations, the processor 430 is configured to analyze the thermal image data acquired by the thermal imaging camera 400. The processor 430 can continue to analyze the thermal image data and, in the event that a thermal anomaly is present in the thermal image data, the processor 430 can take an action to alert a system operator of the anomaly, e.g., via communication to an external device (e.g. 360), sounding an alarm, or the like. For instance, in a simple example, the processor 430 can compare the thermal image data to threshold values and take action if any part of the thermal image data exceeds a threshold.

As described elsewhere herein, in some examples, a thermal imaging camera 400 can be fixed proximate the equipment under test 404 so that regions in thermal image data generated by the thermal imaging camera (e.g., pixels or groups of pixels) consistently correspond to particular regions of the target scene (including the equipment under test 404). That is, in each acquired thermal image, corresponding regions in each thermal image will be representative of substantially the same portion of the target scene.

In some instances, the camera can be equipped with image registration capabilities, such as those described in U.S. patent application Ser. No. 12/196,433, filed Aug. 22, 2008, which is assigned to the assignee of the instant application and is hereby incorporated by reference in its entirety. Such image registration techniques can be used to align any acquired images, for example, to perform comparative analysis between images. Additionally or alternatively, the registration techniques described can be used to register visible light and thermal image data offset due to parallax error. Accordingly, in some such examples, when comparing the thermal image data to a threshold, different regions of the thermal image data (e.g., different pixels) can be compared against different thresholds depending on the portion of the equipment corresponding to each region.

In some embodiments, a thermal imaging camera can include or be in communication with a memory 432 comprising one or more statistical thermal profiles of the target scene. The statistical thermal profiles of the target scene can include, for example, an average temperature value for each of a plurality of regions in the target scene, the standard deviation of the temperature at each region in the target scene, and/or other statistical parameters associated with the target scene. The statistical thermal profile can include statistical parameters associated with a plurality of regions (e.g., pixels) within the target scene and/or with the target scene as a whole (e.g., overall average temperature, etc.). Accordingly, in some such examples, the thermal imaging camera is configured to capture a thermal image of the target scene and compare the captured thermal image to the statistical thermal profile of the target scene.

Comparing a thermal image to a statistical thermal profile can be performed in a variety of ways. In some embodiments, for each region in the thermal image, the absolute difference between the thermal image data and the average temperature in the statistical thermal profile is determined. In some such examples, if the absolute difference exceeds a threshold, the processor takes action to alert the system operator of an anomaly. Similarly, the thermal image data can be analyzed with respect to the average temperature and standard deviation in the statistical thermal profile. In some such examples, if the thermal image data in a particular region is more than a threshold number of standard deviations away from the average, the processor can act to alert the system operator of an anomaly. In some examples, alerting the user comprises indicating the region(s) in the target scene in which the anomaly is present, such as visually indicating the region(s) on a display, for instance, on an external device in communication with the processor. Visual indications can include presenting the region(s) in a predetermined color, flashing such regions, or other ways of visually distinguishing such regions. Some visual presentation schemes can be similar to the visual presentation of alarm conditions such as described in U.S. patent application Ser. No. 11/294,752, filed Dec. 5, 2005, which is assigned to the assignee of the instant application and is hereby incorporated by reference in its entirety.

In the illustrated example of FIG. 4, the thermal imaging camera 400 is in communication with the memory 432 via processor 430. In some such examples, the processor 430 can facilitate transferring thermal image data to memory 432 for comparison to a statistical thermal profile also stored in memory 432. Additionally or alternatively, the processor 430 can carry out the comparison between the statistical thermal profile and the thermal image data. In some embodiments, the processor 430 can store a thermal image in a buffer memory (e.g., a rolling buffer comprising one or more thermal images at a time) for comparison with a statistical thermal profile stored in memory 432. In some such examples, the processor 430 can be configured to save the thermal image in the event that an anomaly is detected based on the comparison, and to discard the image from the buffer if no anomaly is detected. This can reduce memory requirements for the system. In some such embodiments, images saved based on a detected anomaly can be saved in memory 432 and/or communicated to additional or alternative memory. For example, thermal images comprising detected anomalies can be communicated to an external device for storing anomalous thermal images and/or to more quickly alert a user of the detected anomaly. In some such examples, action taken by the processor in the event of a detected anomaly comprises communicating the anomalous thermal image to a system operator (e.g., to the operator's computer, smartphone, tablet, etc.) via wired or wireless communication to alert the operator of the anomaly and to provide a visual representation of the detected anomaly.

Depending on the equipment under test, thermal profiles that are considered "normal" might vary depending on operating parameters of the equipment. For instance, parameters such as the load on equipment, current flowing through the equipment, ambient temperature, equipment on/off status, day/night status and/or time of day, time elapsed since the equipment was powered on, average values such as an average current and/or duty cycle over a period of time, and/or the like can impact what can be considered acceptable thermal behavior of the equipment. In an exemplary embodiment, equipment under test having a high current draw will operate at a higher normal operating temperature when compared to operation at a lower current level. Such parameters may be available via an auxiliary measurement device configured to generate measurement data representative of one or more parameters associated with the target scene and/or the equipment under test.

Accordingly, in some embodiments, statistical thermal profiles can include or otherwise be associated with other attributes of the equipment under test, such as measurement data from an auxiliary measurement device. For example, in some embodiments, different statistical thermal profiles are associated with different values of measurement data acquired from an auxiliary measurement device (e.g., 310). Thus, in some such examples, comparing a thermal image to a statistical thermal profile of a scene further comprises selecting the proper statistical thermal profile according to the additional parameters associated with the equipment under test and a plurality of selectable statistical thermal profiles.

Referring back to FIG. 3, in an exemplary embodiment, thermal imaging camera 300 is configured to acquire thermal image data of equipment under test 304 for comparison to a statistical thermal profile stored in a memory as described elsewhere herein. Comparison to the statistical thermal profile can be performed, for example, by the thermal imaging camera 300, the external device 360, or the auxiliary measurement device 310. The auxiliary measurement device 310 can provide measurement data corresponding to one or more parameters of the equipment under test 304 which may have an impact on the thermal profile of the equipment 304. The measurement data from the auxiliary measurement device 310 can be used to select the appropriate statistical thermal profile to which to compare the acquired thermal image data.

For example, in an exemplary implementation, the external device 360 comprises memory storing a plurality of statistical thermal profiles for the equipment under test 304 and a processor. The external device 360 receives measurement data from the auxiliary measurement device 310 corresponding to the amount of current being drawn by the equipment 304 and thermal image data from the thermal imaging camera 300. The external device 360 can be configured to, via the processor, select the statistical thermal profile corresponding to the received measurement data and compare the received thermal image data to the selected statistical thermal profile. For example, the external device 360 may select a first statistical thermal profile if the measured current is between 0 and 3 amps, a second statistical thermal profile if the measured current is between 3 and 4 amps, and a third statistical thermal profile if the measured current is between 4 and 5 amps.

As described elsewhere herein, the selected statistical thermal profile can be compared to the captured thermal image data for detecting anomalies in the thermal image data. For example, each of a plurality of regions in the thermal image data can be compared to a corresponding region in the selected statistical thermal profile. Comparisons can include comparing the thermal image data to an average value, such as using an absolute difference or determining the number of standard deviations from the mean. Additionally or alternatively, comparisons can include comparing the thermal image data to median values and/or percentile information. For instance, comparisons can include determining, for a given region, the range of temperatures the thermal image data is between for a given percentage of time. Similarly, comparisons can include, for example, determining the percentage of time that the thermal image data falls within a certain temperature of range.

In some embodiments, comparisons can be performed using the external device 360. As described elsewhere herein, in some embodiments, the result of the comparison can be presented on a display 308, for example, visually emphasizing regions in the thermal image data that show significant degrees of anomalousness with respect to the statistical thermal profile. As shown in FIG. 3, the display is in communication with the external device 360. Thus, the external device 360 can be configured to generate a visual representation based on the comparison and output the representation on the display 308. In various such embodiments, the display 308 can be a standalone display in communication with the external device 360 or can be integrated into the external device 360.

It will be appreciated that a variety of alternatives are possible. For example, the auxiliary measurement device 310 can be configured to measure parameters other than or in addition to the current drawn by the equipment 304. The processor, memory, and/or display described as being present in external device 360 can instead be in one or both of the thermal imaging camera 300 and the auxiliary measurement device 310. Such a device can perform the statistical analysis (e.g., comparisons to the statistical thermal profile) and can similarly include and/or be in communication with display 308 for the visual presentation of the results of the analysis. Additionally, any number of measurement-data-dependent statistical thermal profiles may be selectable based on any number of a variety of parameters measureable via one or more auxiliary measurement devices (e.g., 310).

In some examples, any number of parameters can be used to designate which statistical thermal profile is used for comparison with the thermal image data. For example, one or more auxiliary measurement devices 310 can be used to provide measurement data representative of a plurality of parameters. The plurality of parameters can be used to determine which statistical thermal profile to compare to the thermal image data. In some examples, each of the plurality of parameters corresponds to a coordinate in an n-dimensional lookup table indexing each of the selectable statistical thermal profiles. The aggregate coordinates of each of the plurality of parameters can indicate which of the plurality of statistical thermal profiles is most appropriate for comparing to a thermal image of the current state of the equipment under test. In some alternative examples, rather than fitting the parameters to an existing profile, a statistical thermal profile can be interpolated from existing statistical thermal profiles to fit the plurality of parameters. That is, in some embodiments, a statistical thermal profile can be generated based on the received measurement data based on interpolation and/or extrapolation between and/or beyond existing statistical thermal profiles.

In some embodiments, the thermal image data for comparison with the statistical thermal profile is acquired substantially simultaneously with the measurement data used to select the appropriate statistical thermal profile for comparison. In this way, the parameters used for selecting the statistical thermal profile are the parameters representative of the equipment under test while the thermal image data is captured.

Figure 5:
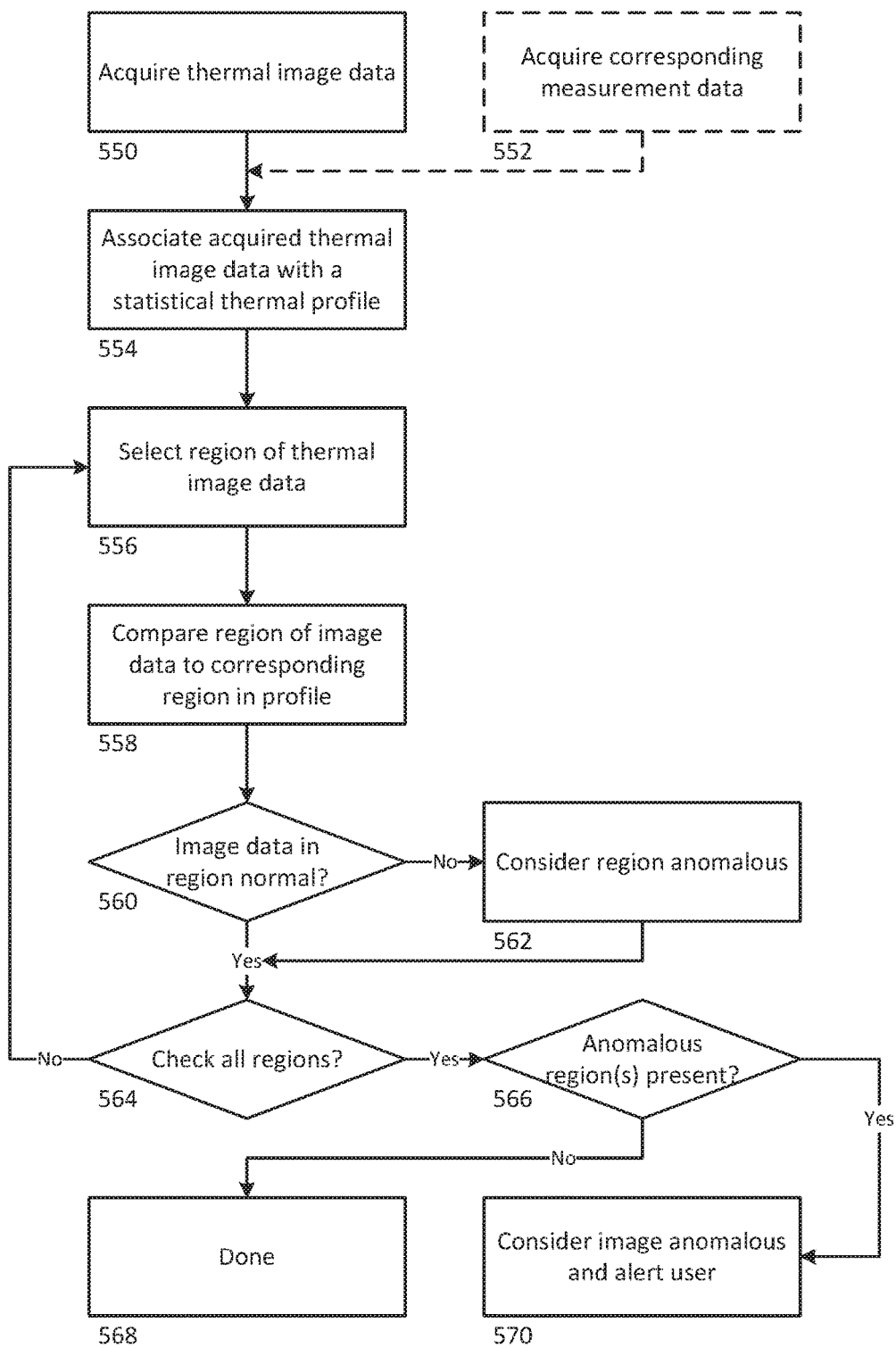
FIG. 5 is a process flow diagram illustrating an exemplary method for detecting and alerting a user of an anomaly in a thermal image.

FIG. 5 is a process flow diagram illustrating an exemplary method for detecting and alerting a user of an anomaly in a thermal image. In the illustrated example, the method includes acquiring thermal image data of equipment under test (550) and associating the acquired thermal image data with a statistical thermal profile (554). The method includes the steps of selecting a region of thermal image data from the thermal image (556) and comparing the selected region of data to a corresponding region in the statistical thermal profile (558). As described elsewhere herein, such a comparison can include any number of statistical comparisons, such as comparing the thermal image data from the selected region to an average value in the statistical thermal profile.

Based on the comparison, the method can include determining whether or not the image data in the given region is normal (560). Determining normalness can include, for example, determining if the image data is within a predetermined number of standard deviations from the mean when compared to the statistical thermal profile. Other determining steps can be performed as described elsewhere herein. If the image data in the region is not normal (e.g., is not within the predetermined number of standard deviations from the mean, is not within the range in which it lies a predetermined percentage of time, etc.), then the region is considered anomalous (562). After determining whether or not the image data in the region is normal (560), if not all regions have been checked (564), then a new region can be selected (556) and compared to the corresponding region in the statistical thermal profile (558). It will be appreciated that, while the process includes the step of determining whether or not all regions have been checked (564), such a step need not be applied to an image as a whole. For instance, in some examples, only a subset of regions of thermal image data are representative of the equipment under test. Accordingly, in some examples, a user may specify a region of interest (ROI) for monitoring thermal image data and comparing to a statistical thermal profile. Thus, in some embodiments, determining whether or not all regions have been checked (564) can comprise determining whether or not all regions of interest have been checked. In various examples, a user may select an ROI via a user interface. In other embodiments, a camera may select an ROI based on a detected image feature, such as thermal features, detected edges, and the like.

It will be appreciated that, while shown as a looping process in which each region is individually selected and analyzed with respect to the statistical thermal profile, in some embodiments, a plurality of regions, and in some cases, all regions, can be analyzed with respect to the statistical thermal profile substantially simultaneously. For instance, rather than looping through each region, whole-image analysis processes can be employed for determining whether the image data in each analyzed region is considered normal or anomalous (560).

Once each region of interest has been analyzed (564), if there are no anomalous regions present in the image data (566), the analysis of the image may be stopped (568). In various examples, images showing no anomalous regions can be discarded, saved in a temporary buffer memory, or exported to an image archive, though other options are also possible. If there are anomalous regions present in the image data (566), the thermal image can be considered anomalous and a user can be alerted of the occurrence of the anomalous image (570). As described elsewhere herein, alerting the user (570) can be done in a variety of ways, including audible and/or visible alerts being presented to the user via a user's external device (e.g., smartphone, tablet, computer, etc.). In some examples, a visual alert can include an image indicating which regions in the image are considered anomalous (e.g., as in step 562). Additionally or alternatively, the visual alert can include measurement data from one or more corresponding auxiliary measurement devices (e.g., as acquired in step 552).

In some alternative embodiments, there is not necessarily a binary "anomalous or not" distinction, but rather the user can be alerted of the degree of anomalousness in view of the statistical thermal profile in each region of the thermal image data. For instance, such a visual representation of degrees of anomalousness in view of the statistical thermal profile can be generated and subsequently presented to a user showing the degree of anomalousness in each region. In some cases, a region can be considered "anomalous or not," and can further include representation of the degree of determined anomalousness in each region considered to be anomalous. For example, in some embodiments, in the event that a region in the region satisfies a predetermined requirement (e.g., considered anomalous), an image representation of the degree of anomalousness can be generated and presented to a user. In some such examples, after associating the acquired thermal image data with a statistical thermal profile (554), an "image" comprising the degree of anomalousness in each region can be generated and analyzed. If the anomalousness in any region is determined to exceed a predetermined requirement, the thermal image can be considered anomalous and a user can be alerted (570). In some such examples, the "image" comprising the degree of anomalousness in each region can be presented to the user as a part of the alert, and in some embodiments, along with corresponding measurement data.

Such an example does not necessarily require region-by-region analysis in order to detect anomalies in the thermal image data. As such, it will be appreciated that various steps in the exemplary method of FIG. 5 can be omitted and/or permuted without departing from the scope of this disclosure. In general, a variety of similar methods can be performed to effectively carry out the similar processes (e.g., determining regions comprising thermal anomalies) without explicitly following the steps of FIG. 5 in the exemplary order presented.

The exemplary method of FIG. 5 can be repeated periodically to provide routine inspection of the behavior of equipment under test. In some embodiments, a user can customize a schedule so that a new thermal image is acquired and analyzed for anomalies according to the custom schedule. Additionally or alternatively, the system can be configured to perform such a process in response to detected changes in system behavior. For example, in some embodiments, the thermal imaging camera can operate in a monitoring mode in which images are not necessarily saved or compared to statistical thermal profiles. Rather, images are analyzed for certain conditions. Such conditions can include thermal image data, temperatures detected therein, and/or rates of change thereof meeting a threshold value. If the images do not meet such conditions, the images are discarded and the camera continues operating in the monitoring mode. However, in some such embodiments, when the image(s) do satisfy such criteria, the method of FIG. 5 can be initiated to perform an anomaly detection process.

Additionally or alternatively, measurement data from an auxiliary measurement device can be used to trigger an image acquisition and anomaly detection process such as the one described in FIG. 5. In an exemplary embodiment, a current flow sensor can monitor the current flowing to equipment under test. Spikes or other changes in the measured current can initiate an anomaly detection process. Similarly, an auxiliary measurement device including contact temperature sensor can be used to observe local temperature changes related to the equipment under test, which may provide an indication of increased anomaly likelihood and can initiate an anomaly detection process. Various examples are possible. In some embodiments, certain observations of system behavior can generally trigger additional system operation (e.g., thermal anomaly detection) such as described in U.S. patent application Ser. No. 14/856,046, filed Sep. 16, 2015, which is assigned to the assignee of the instant application and which is hereby incorporated by reference in its entirety.

Figure 6:
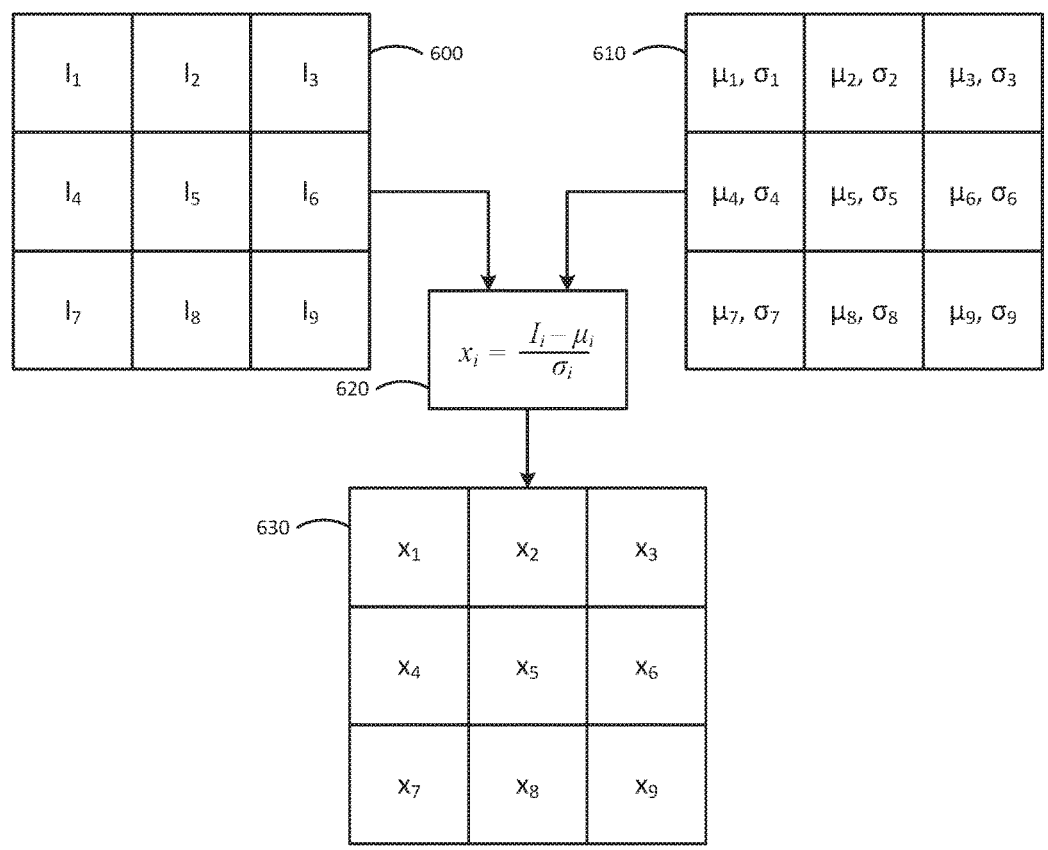
FIG. 6 is a schematic diagram illustrating generating such a visual representation according to some examples.

As described elsewhere herein, in some examples, alerting a user of a detected anomaly can include presenting an image to a user representing the degree of anomalousness of the thermal image data in view of the statistical thermal profile. FIG. 6 is a schematic diagram illustrating generating such a visual representation according to some examples. As shown, a captured thermal image 600 comprises a plurality of regions of thermal image data each represented by intensity $I_i$.

According to the exemplary embodiment of FIG. 6 and the corresponding description, the intensity $I_i$ can correspond to the amount of power emitted by the target scene and received at a corresponding portion of a thermal imaging device, the detected temperature associated with that region, or the like. In some embodiments, each region corresponds to a pixel of captured thermal image data. In other examples, each region corresponds to a plurality of pixels. Processing regions comprising a plurality of pixels rather than each pixel individually can save memory and processing resources. In some such examples, the intensity $I_i$ in a region corresponding to a plurality of pixels is representative of an average received power or temperature of the pixels associated with that region.

As discussed elsewhere herein, the thermal image 600 can be compared to a statistical thermal profile 610 for detecting possible anomalies in the thermal image data. The statistical thermal profile 610 of FIG. 4 comprises a plurality of regions corresponding to the plurality of regions in the thermal image 600. In the illustrated example, each of the plurality of regions in the statistical thermal profile comprises an average value ($\mu_i$) and a standard deviation ($\sigma_i$).

In general, for each region, the intensity value in the thermal image data is some number of standard deviations away from the average value in the statistical thermal profile 610 as illustrated in Equation 1 below:

$$I_i = \mu_i \pm x_i \sigma_i \quad (1)$$

wherein:

$I_i$ is the intensity in region i in the thermal image data, $\mu_i$ is the average value associated with region i in the statistical thermal profile, $\sigma_i$ is the standard deviation associated with region i in the statistical thermal profile, and $x_i$ is the number of standard deviations from the intensity value is from the average value in the statistical thermal profile in region i.

In an exemplary embodiment, a processor (e.g., 430) can be configured to determine, for each region, the number of standard deviations the intensity value is from the average value in the statistical thermal profile 610, $x_i$, for example, via Equation 2 below:

$$x_i = I_i - \mu_i / \sigma_i \quad (2)$$

The set of $x_i$'s calculated for each of the plurality of regions in the thermal image data 600 and statistical thermal profile 610, such as via an equation 620, can be used to generate anomaly data, which may be used to generate an anomaly image 630 comprising anomaly image data. Accordingly, the anomaly data, and similarly, the anomaly image data 630 provides a view of how "normal" or "abnormal" each region in the thermal image data is compared to the statistical thermal profile. In some examples, the anomaly image 630 is palettized according to a false color palette in which a user can quickly observe the thermal behavior in various regions in a target scene (e.g., equipment under test) relative to typical behavior reflected in the statistical thermal profile. For example, each region of the anomaly image 630 can be represented by a color corresponding to the number of standard deviations from the mean for the thermal image data is for the given region. In an exemplary embodiment, regions within two standard deviations of the mean can be shown as green, regions between two and three standard deviations from the mean can be shown as yellow, and regions outside of three standard deviations from the mean can be red. Other palettization schemes are possible, including schemes using fewer or more colors representative of fewer or more discrete characterizations of the anomaly data.

In addition to or in lieu of color representations, other visual indications can be used to represent normal or abnormal regions. For instance, in some examples, regions having thermal image data meeting a predetermined requirement (e.g., a predetermined number of standard deviations from the mean in the statistical thermal profile) can be displayed as flashing in the anomaly image. In some such embodiments, the rate of flashing in the anomaly image can be representative of the number of standard deviations from the mean the thermal image data is in the corresponding region.

In some embodiments, in the event that the magnitude of a region in the anomaly image 630 meets a predetermined requirement (i.e., when the thermal image data in a region is sufficiently anomalous with respect to the corresponding region in the statistical thermal profile), a processor (e.g., 430) can act to alert a user of the excessive deviation. In some such examples, the alert comprises displaying a display image on a display (e.g., 408) that comprises anomaly data.

Anomaly data, such as in anomaly image 630, can be included in such a display image in a variety of ways. In some embodiments, the anomaly image data can be blended with one or more image data streams to provide additional context to a user viewing the image. For instance, in some examples, the anomaly image data can be alpha-blended with the corresponding thermal image data of the target scene for presentation on a display. Alternatively, the anomaly image data can be blended with visible light image data representative of the target scene, allowing the user to more easily associate thermal behavior compared to the statistical thermal profile at physical locations of an object of interest shown in the visible light image data. In still further embodiments, the anomaly image data can be blended into a combination visible light and thermal image, such as blended thermal and visible light images, picture-in-picture thermal and visible light image configurations, and other known display modes.

In some embodiments, a processor (e.g., 430) can perform feature detection processes (e.g., edge detection) on received thermal image data and/or visible light image data. In some such examples, the processor can generate an image that includes enhanced and/or emphasized features, such as edges, based on analysis of thermal image data and/or visible light image data. Exemplary feature enhancement is described in U.S. patent application Ser. No. 14/837,757, filed Aug. 27, 2015, which assigned to the assignee of the instant application and is incorporated by reference in its entirety.

In some embodiments, such a modified image including enhanced features can be blended with the anomaly image data in order to provide additional context to a user of the target scene, such as physical edges or boundaries in the image which may be unperceivable in the anomaly image data alone. In still further embodiments, the detected edges or other features from one or both of the thermal and visible light image data can be blended or overlaid onto the anomaly image data without blending the entirety of the anomaly image data with other data (e.g., thermal or visible light image data at locations not including such detected features).

It will be appreciated that a variety of options are possible for blending anomaly image data with other data streams. In some examples, the amount of blending of the anomaly image data with other data streams can be dependent on the amount of anomalousness in the anomaly data in a particular region (e.g., with respect to Equations 1 and 2, $x_i$ in region i). For instance, in some examples, the amount of anomaly image data blended into the displayed image at each region increases with the magnitude of the anomaly data in that region. Accordingly, in such blending schemes, the regions in the image that are the most anomalous (e.g., are the greatest number of standard deviations from the average value in the statistical thermal profile, are the furthest outside of a thermal range achieved a certain percentage of the time, etc.) include the greatest percentage of anomaly image data in order to emphasize anomalous regions to the user.

In some embodiments, anomaly image data is blended into other data streams when the anomaly data satisfies a predetermined condition. For instance, in some examples, the anomaly image data is only blended into another data stream in regions in which the magnitude of the anomaly data exceeds a predetermined threshold. For example, in an exemplary embodiment, with reference to FIG. 5, only regions considered anomalous per step 562 are combined with other data streams. In such an embodiment, in the event that an image is considered anomalous (e.g., step 570), alerting the user comprises presenting an image to the user comprising a first data stream (e.g., thermal and/or visible light image data) and, in the regions considered anomalous, anomaly image data.

As described herein, acquired image data can be compared to a statistical thermal profile to detect anomalies in the thermal image data. In various examples, statistical thermal profiles can be stored in memory, for example, of a camera, auxiliary measurement device, external device, remote facility, or the like, and accessed upon performing an anomaly detection process. In some embodiments, a thermal imaging camera fixed proximate equipment under test can be used to generate the statistical thermal profile. For instance, in some examples, the camera can be configured to periodically acquire thermal images of the equipment under test and generate the statistical thermal profile based on the acquired thermal images. In some such examples, the images used to generate the statistical thermal profile are acquired when the equipment under test is known to be in good operating condition, such as equipment that is new or has been recently serviced or inspected. Averages, medians, standard deviations, percentile analysis, and/or other statistical parameters from a plurality of regions in the acquired thermal images can be determined and used to generate the statistical thermal profile.

In some examples, the thermal imaging camera stores each acquired thermal image used for generating the statistical thermal profile in memory 432. The stored images can be aggregated over a period of time in an image database and used to generate the statistical thermal profile. In some such examples, the memory storing the image database is included in the camera. Alternatively, the memory can be in an external device (e.g., 360), such as an external computer or server, in communication with the thermal imaging camera.

In some embodiments, acquired thermal images can be stored in the image database and, once enough images are acquired, the images can be analyzed to generate the statistical thermal profile. In some examples, the camera acquires a specific number of images used for generating the statistical thermal profile. The images can be acquired according to an image acquisition schedule, such as once per hour, once per day, or the like. Once the requisite number of images is acquired, the images can be processed for generating the statistical thermal profile of the scene.

Figure 7:
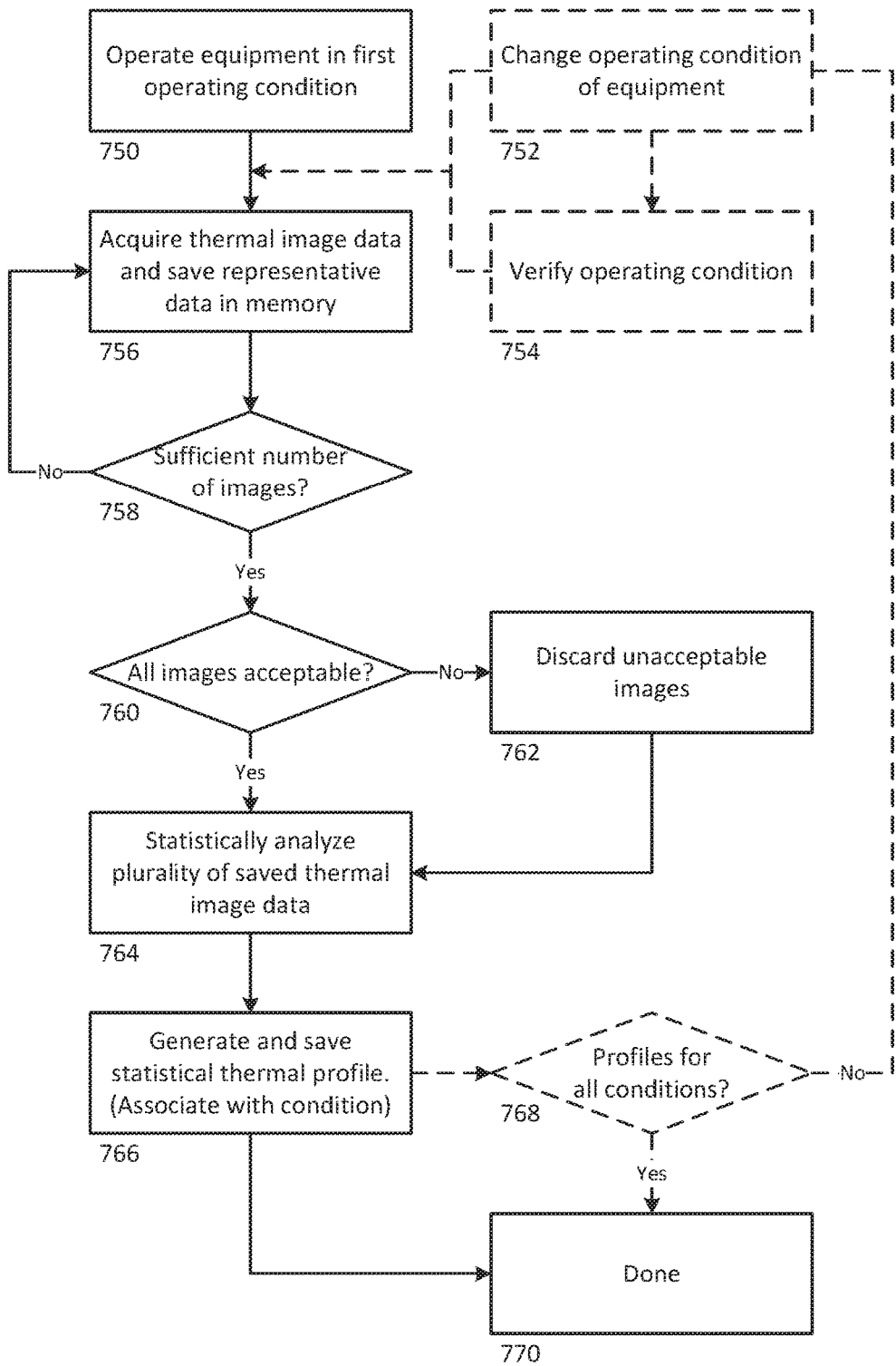
FIG. 7 is a process-flow diagram illustrating an exemplary process for generating a statistical thermal profile according to some embodiments.

FIG. 7 is a process-flow diagram illustrating an exemplary process for generating a statistical thermal profile according to some embodiments. In the method of FIG. 7, equipment under test can be operated in a first operating condition (750). The first operating condition can be a known condition, such as new, recently serviced, or the like. Additionally or alternatively, the first operating condition can be based on an operating parameter of the equipment, such as an ambient temperature, a current draw, or the like. In some examples, the method can include the step of verifying the operating condition (754), for example, via an auxiliary measurement device.

When the equipment is operating in the first operating condition (750), a thermal image data of the equipment is acquired and representative data is saved in memory (756). Images can be acquired and analyzed accordingly until a sufficient number of images for generating a statistical thermal profile have been acquired (758). In some embodiments, acquired image data can be analyzed to determine which images are acceptable (760). For example, in some embodiments, the images used to generate the statistical thermal profile are stored in memory (e.g., in camera memory or in an external memory such as in an external device) where they are viewable by a user. The user can inspect the thermal images that are used to generate the statistical thermal profile and manually exclude any undesirable images from the profile. For example, if, as a thermal image is being captured, a person walks between the camera and the equipment under test, the thermal data from that image might not be useful in generating a statistical thermal profile of the equipment under test. Thus, the user inspecting the images used to generate the statistical thermal profile may manually eliminate this image from the analysis. Additionally or alternatively, an automated process can be used to detect unacceptable images, such as if thermal image data in a region is significantly different from the thermal image data in that region in a previous thermal image. When one or more images are deemed unacceptable, such images can be discarded (762).

The image data from acceptable thermal images can be statistically analyzed (764) in order to generate and save a statistical thermal profile (766). As described elsewhere herein, statistical analysis can include determining, for each of a plurality of regions, average values, standard deviations, or other statistical parameters to generate the statistical thermal profile. In some embodiments, the saved statistical thermal profile can be associated with the operating condition (e.g., the first operating condition) for comparison to future thermal images of equipment under test operating in a similar condition.

In some embodiments, a plurality of statistical thermal profiles can be generated associated with a plurality of different operating conditions. Steps associated with an exemplary process for generating a plurality of statistical thermal profiles associated with different operating conditions are shown in broken lines. In some embodiments, after generating and saving a statistical thermal profile (766), a decision can be made whether or not statistical thermal profiles for all desired conditions are generated (768). Such a decision can be made by a user overseeing statistical thermal profile generation or can be automated, for example, using a processor with instructions for generating a predetermined number or set of statistical thermal profiles. If all desired statistical thermal profiles are generated, the statistical thermal profile generation process is complete. Otherwise, the process can proceed to change the operating condition of the equipment under test (752) and the process repeats. In some embodiments, feedback measurement data from an auxiliary measurement device can be used to verify the new operating condition (754) prior to generating the statistical thermal profile associated with the new operating condition.

In some examples, a system can more passively generate and/or update statistical thermal profiles associated with different operating conditions. For example, a system can generally monitor the operating condition of a piece of equipment under test. For any of a variety of reasons, the operating condition of the equipment may change naturally (752). For example, the ambient temperature of outdoor equipment may change between night and day and/or between seasons. In some such circumstances, in some embodiments, verifying the operating condition (754) can include the step of determining the operating condition and verifying which statistical thermal profile is most closely associated with the current operating condition. Then, acquired thermal image data (e.g., from step 756) can be used to generate and/or update the statistical thermal profile associated with the determined operating condition.

It will be appreciated that the process illustrated in FIG. 7 is exemplary and suitable alternatives are possible. For instance, other methods can be performed in which one or more steps of FIG. 7 are permuted or eliminated. In some examples, the representative data (e.g., collected in step 756) comprises the entire thermal image data itself. In other examples, statistical data is taken from the thermal image data and combined with similar previously-acquired data to update a statistical thermal profile in the memory, and the image data itself is discarded. For example, the memory can maintain a running average value and standard deviation for each of a plurality of regions of thermal image data. When new thermal image data is acquired (e.g., at step 756), thermal image data from the image is used to update the statistical parameters in each of the regions and the image is discarded to preserve memory. In some such embodiments, generating a statistical thermal profile (step 766) might be performed prior to acquiring each set of thermal image data (e.g., step 756) used in generating the statistical thermal profile.

In other examples, the statistical thermal profile can be continually generated and updated as additional images are acquired. In such embodiments, even after a statistical thermal profile is established, subsequently acquired thermal images can be aggregated with the previous statistical thermal profile to update the statistical thermal profile. Thus, in some examples, the statistical thermal profile evolves over time as additional images are acquired during anomaly detection processes. In some such examples, acquired measurement data can be used to determine which statistical thermal profile is to be updated with acquired thermal image data.

Figure 8:
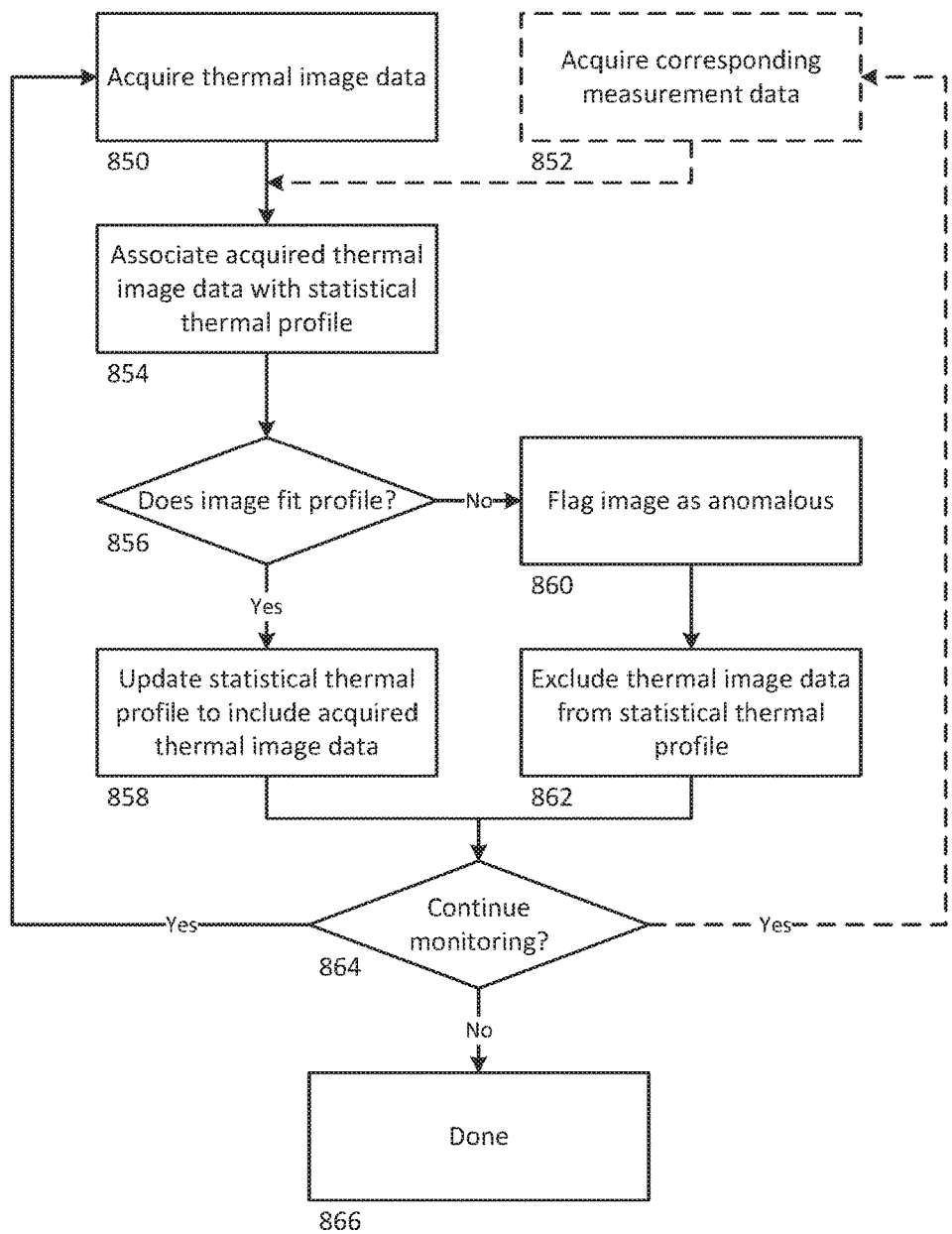
FIG. 8 is a process flow diagram illustrating an exemplary method for continually updating a statistical thermal profile.

FIG. 8 is a process flow diagram illustrating an exemplary method for continually updating a statistical thermal profile. Accordingly to the exemplary method of FIG. 8, thermal image data is acquired (850) and associated with a statistical thermal profile (854). As described elsewhere herein, in some implementations, only a single statistical thermal profile is present and is associated with all acquired thermal image data by default. In other embodiments, the method can include the step (shown in broken lines) of acquiring measurement data corresponding to the acquired thermal image data (852). In such embodiments, the acquired thermal image data can be associated with the statistical thermal profile corresponding to the acquired measurement data (854).

The image data can be compared to the statistical thermal profile to determine whether or not the acquired thermal imaging data fits the statistical thermal profile (856). Such a determination can comprise, for example, determining whether or not, in each of a plurality of regions, the thermal image data falls within a standard deviation (or some other number of standard deviations) of the mean according to the statistical thermal profile. If it is determined that the image does fit the profile, then the statistical thermal profile can be updated to include the acquired thermal image data (858).

However, if the image data does not fit the statistical thermal profile (e.g., determined in step 856), the image can be flagged as anomalous 860. The anomalous image can be treated in a variety of ways (e.g., palettized, presented to a user, etc.) as described elsewhere herein. Rather than updating the statistical thermal profile with the acquired thermal image data, the image data from the anomalous image can be excluded from the statistical thermal profile (862). In some embodiments, the thermal image data is excluded from the statistical thermal profile only in regions in which the thermal image data is considered anomalous. In some examples, the anomalous image can be sent to a user, and the user can decide whether or not to include some or all of the image for updating the corresponding statistical thermal profile.

In an exemplary embodiment, thermal image data is compared region-by-region to a statistical thermal profile. Thermal image data from regions that are within a predetermined number of standard deviations (e.g., within one standard deviation) from the mean value of the corresponding region in the statistical thermal profile are used to update the statistical thermal profile to include the acquired thermal image data in those regions (858). However, regions in the statistical thermal profile corresponding to regions in the thermal image data that are not within the predetermined number of standard deviations from the mean of the statistical thermal profile are excluded from the statistical thermal profile (862). Moreover, the overall image can be flagged as anomalous (860) and processed accordingly.

Various arrangements can be employed for generating one or more statistical thermal profiles as described in the exemplary processes of FIGS. 7 and 8. With further reference to FIG. 4, the auxiliary measurement device 410 can be used in conjunction with the thermal imaging camera 400 for building a plurality of statistical thermal profiles for comparison to captured thermal images. As described elsewhere herein, statistical thermal profiles can be generated in a number of ways according to various embodiments. When the thermal imaging camera 400 is used to generate the statistical thermal profile(s) (e.g., via a profile generation process and/or a continued, dynamic process), measurement data from one or more auxiliary measurement devices 410 can be acquired to determine which statistical thermal profile is updated with a set of captured thermal image data.

For instance, during exemplary operation, the thermal imaging camera 400 can acquire image data of equipment under test 404 for building a statistical thermal profile. Measurement data representative of at least one parameter of the equipment under test 404 can be acquired from the auxiliary measurement device 410 at approximately the same time as the image data. For example, in some embodiments, processor 430 is configured to initiate acquisition of both the image data and the measurement data substantially simultaneously.

The processor 430 can be configured to process the measurement data received from the auxiliary measurement device 410 in order to determine an operating condition of the equipment under test 404. The processor 430 can be further configured to determine, based on the processed measurement data, which of a plurality of statistical thermal profiles corresponds to the measurement data, and associates the corresponding acquired thermal image data with that statistical thermal profile. Once an acquired thermal image data is associated with a statistical thermal profile based on the measurement data, the thermal image data can be used in generating the statistical thermal profile.

In some such embodiments, the equipment under test 404 can be intentionally operated in a constant state corresponding to a single statistical thermal profile (e.g., constant current draw) while a plurality of thermal images of the equipment 404 are captured using the thermal imaging camera. Measurement data from the auxiliary measurement device 410 can be used to ensure that the equipment under test 404 is operating under the correct conditions for generating the desired statistical thermal profile. The acquired images can be stored, for example, in memory 432 (e.g., in camera or elsewhere) as a part of a plurality of images for generating the statistical thermal profile. Once a sufficient number of images have been acquired, the images can be statistically analyzed to generate the statistical thermal profile (e.g., including mean and standard deviation values for a plurality of regions in the images). Once the statistical thermal profile is generated, one or more of the images can be retained, deleted, or transferred to a separate database for reference.

Alternatively, as described elsewhere herein, in some examples, each acquired thermal image need not be stored in memory for statistical thermal profile generation. Instead, in some such embodiments, statistical data from each of a plurality of regions in the thermal image data can be combined with existing statistical data stored in memory 432 and the image data itself can be discarded. Such processes can be repeated for a predetermined number of times (e.g., during an explicit statistical thermal profile generation mode). Alternatively, the statistical thermal profile generation process is continually performed during anomaly monitoring. In some examples, the process of FIG. 7 is performed in order to establish an initial statistical thermal profile based on a minimum number of sets of acquired thermal image data. Once the initial statistical thermal profile is generated, the process of FIG. 8 can be employed to continually update and refine the statistical thermal profile over time.

In various profile generation processes, a plurality of sets of thermal image data can be captured based on a variety of acquisition schedules and/or other criteria for generating a statistical thermal profile. In some embodiments, a processor can initiate the capturing of thermal image data (and in some embodiments, associated measurement data) according to specific time intervals (e.g., once per day, once per hour, etc.). Additionally or alternatively, a processor can be configured to acquire additional thermal image data in the event of changes detected, for example, by the thermal imaging camera and/or additional devices such as one or more auxiliary measurement devices in communication with the processor. In still further examples, the capture rate can be adjusted based on sensed parameters of the target scene, such as frame-to-frame temperature differences in each region and the like. For instance, if the rate of temperature change is low, the image capture rate can be reduced. In the event of an increase in the rate of temperature change, the image capture rate can be increased likewise.

In some examples, the thermal imaging camera can enter a "sleep mode" to conserve power between image acquisition times. In some such examples, certain aspects of the system are kept active in a monitoring mode to detect possible issues, such as an auxiliary measurement device communicating with a processor.

In some examples, profile generation processes and/or anomaly detection processes can be customized according to the demands of the system and the resources available for acquiring data. With reference to FIG. 4, in some examples, memory 432 (e.g., in the thermal imaging camera 400, auxiliary measurement device 410, or an external device) is sufficiently large to store a plurality of thermal images for generating the statistical thermal profile. In some embodiments, memory 432 includes such images until the statistical thermal profile is created, and such images can be discarded. Additionally or alternatively, memory 432 can store any number of images captured for anomaly detection.

For example, in some embodiments, every image captured by the thermal imaging camera may be stored in the memory 432 for future recall. In other embodiments, only images flagged as anomalous are stored in memory 432. In some embodiments, a rolling buffer of image data stores a predetermined number of thermal images, and when a new image is captured, the oldest image in the buffer is replaced by the new image. In some such examples, anomalous images are stored separately from the buffer so that such images are not inadvertently deleted without a user observing the anomaly. In various embodiments, thermal image data can be uploaded from the camera to an external device or a remote location for more long-term storage without taking up memory resources of the camera. For instance, in some examples, anomalous images are uploaded for long-term storage. In some embodiments, anomalous images are stored in combination with a sequence of images captured before and/or after the anomalous image to allow a user to observe trends in the target scene before and/or after the detected anomaly.

As described elsewhere herein, in some embodiments, thermal image data is not necessarily retained in memory for purposes of statistical thermal profile generation. In some examples, the thermal image data is used to update the statistical thermal profile before the image data is discarded. Additionally or alternatively, statistically important values can be retained in memory and/or used to update a statistical thermal profile while the captured thermal image data is discarded. For example, in some embodiments, sums and sums of squares of thermal image data can be updated in each of a plurality of regions when a new thermal image is captured and the image itself can be discarded. Thus, properties such as mean values and standard deviations can be calculated from a series of acquired thermal images without the need for retaining memory-consuming image files. This can reduce specification requirements (e.g., memory capacity) and enable the implementation of a low-cost camera.

While described in some embodiments as employing a fixed camera proximate equipment under test, in other examples handheld thermal imaging cameras can be used to carry out a similar process via a manual inspection. For example, an operator of a handheld thermal imaging camera can be directed to capture one or more thermal images of a scene from a known position to substantially recreate a previously-captured image. Some such processes are described in U.S. patent application Ser. No. 13/331,644, field Dec. 20, 2011, and U.S. patent application Ser. No. 13/336,607, filed Dec. 23, 2011, each of which is assigned to the assignee of the instant application and is hereby incorporated by reference in its entirety.

Via such or similar processes, a user of a handheld thermal imaging camera can capture a plurality of images from substantially the same vantage point in order to generate a statistical thermal profile and/or to perform anomaly detection processes as herein described. In some examples, during an anomaly detection process, one or more statistical thermal profiles can be selected from the camera's local memory. Additionally or alternatively, the camera can be used to download or stream one or more statistical thermal profiles from an external device (e.g., a camera, a computer, a remote server, etc.) for performing an anomaly detection process using the handheld camera. In some embodiments, one or more statistical thermal profiles accessible by the camera can be provided by an equipment manufacturer, such as downloaded from a manufacturer's website or provided by the manufacturer during equipment delivery and/or installation. For example, a manufacturer may perform testing and/or analysis of the equipment at the factory that comprises creating one or more statistical thermal profiles associated with the equipment under one or more operating conditions.

In some embodiments, a statistical thermal profile accessible by a user of a handheld camera can have been previously generated via a separate camera deployed proximate equipment under test using methods such as those described elsewhere herein. The camera can store the statistical thermal profile and/or upload the statistical thermal profile to a server or other external device. A user of a handheld camera can acquire the statistical thermal profile from the server or other external device prior to inspection. In some embodiments, if the deployed camera is still in place proximate the equipment under test, the handheld camera can interface directly with the deployed camera (e.g., via a wireless connection) to receive the statistical thermal profile. In some such embodiments, the deployed and/or handheld cameras can communicate with one or more other auxiliary measurement devices proximate the equipment under test in order to select the appropriate statistical thermal profile for performing the analysis.

In a variety of such examples, the handheld camera can be configured to compare acquired thermal image data to a statistical thermal profile as described elsewhere herein to detect the presence of one or more anomalies in the acquired thermal image data. The handheld camera can indicate to the user the presence and/or location of anomalies in the image, such as via an audible alert and/or a visual alert such as described elsewhere herein.

Example thermal image cameras and related techniques have been described. The techniques described in this disclosure may also be embodied or encoded in a computer-readable medium, such as a non-transitory computer-readable storage medium containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), a hard disk, optical media, or other computer readable media. Additionally or alternatively, processing techniques as described herein could be implemented by way of FPGAs.

For example, an external computer comprising such computer readable medium can receive thermal image data from a thermal imaging camera or from memory and perform anomaly detection processes such as those described herein. In some embodiments, various portions of the techniques can be embodied in multiple components. For example one or more auxiliary measurement devices can be used for generating and/or selecting an appropriate statistical thermal profile based on the operating conditions of the equipment under test. It will be appreciated that, while examples herein are described with reference to equipment under test, various embodiments described herein may be implemented using parameters associated with the target scene represented in the thermal image data. For instance, statistical thermal profiles can be selected associated with an ambient temperature associated with the entire scene, the time and/or date the image data representative of the target scene is captured, and the like. Additionally or alternatively, parameters representative of the target scene can include those of equipment represented in the image of the target scene, such as a current drawn by equipment represented in the thermal image data.

In some embodiments, a first thermal imaging camera can be used to generate one or more statistical thermal profiles. The statistical thermal profiles can be stored in the camera or on an external device and/or server for access by other cameras for performing anomaly detection processes. Anomaly data can be used to construct display images indicating regions of the target scene in which thermal anomalies are present, and the severity of such anomalies. Such image generation can be performed on an inspection camera (e.g., using one or more statistical thermal profiles) or on an external device capable of communicating with an inspection camera.

In further examples, embodiments of the invention can be embodied in a display system. The display system can be configured to receive visible light and thermal image data and carry out processes such as those herein described. Exemplary display systems can include one or more processors, a display and a user interface for carrying out such processes. A display system can be incorporated into any appropriate device or system capable of receiving and processing image data. In some embodiments, the display system can include a portable, hand-held thermal imaging camera such as those described elsewhere herein in order to capture corresponding visible light and thermal images and provide visible light and thermal image data to other components of the imaging system. In further embodiments, the imaging system is fully incorporated into such a camera, or can consist essentially of a camera capable of carrying out any of the various processes described.

Various embodiments have been described. Such examples are non-limiting, and do not define or limit the scope of the invention in any way. Rather, these and other examples are within the scope of the following claims.

The invention claimed is:

1. A thermal analysis system comprising:
a memory comprising a statistical thermal profile representing typical thermal behavior of each of a plurality of regions of a target scene and determined from a plurality of thermal images of the target scene over time;
an infrared (IR) camera module capable of receiving IR radiation from a target scene and generating corresponding thermal image data representative of a heat pattern across the target scene based on the received IR radiation; and
a processor in communication with the memory and the IR camera module and configured to:
receive thermal image data from the IR camera module representative of the heat pattern of the target scene;
for each of the plurality of regions in the received thermal image data, compare the thermal image data of the region to a corresponding region in the statistical thermal profile of the target scene;
generate anomaly image data comprising a plurality of regions, each region in the anomaly image data corresponding to a respective region in the received thermal image data and representative of the degree of anomalousness of the received thermal image data with respect to the statistical thermal profile in that region; and
generate a display image comprising the anomaly image data blended with one or more additional data streams.

2. The system of claim 1, wherein the statistical thermal profile comprises, in each of the plurality of regions, at least two statistical parameters representative of typical thermal image data in the target scene.

3. The system of claim 2, wherein the statistical thermal profile comprises a mean temperature value and a standard deviation for each of the plurality of regions from the plurality of thermal images over time.

4. The system of claim 3, wherein the degree of anomalousness of the received thermal image data with respect to the statistical thermal profile comprises the number of standard deviations the thermal image data differs from the mean temperature value in the statistical thermal profile in each region.

5. The system of claim 4, further comprising a display in communication with the processor, and wherein the processor is further configured to present the display image on the display.

6. The system of claim 1, wherein the one or more additional data streams comprises at least one from the list consisting of:
thermal image data, visible light image data, and modified image data including enhanced features.

7. The system of claim 1, wherein the processor is further configured to:
determine if the received thermal image data is considered anomalous based on the anomaly image data in the plurality of regions; and
if the thermal image data is considered anomalous, save the received thermal image data and/or the generated display image in memory.

8. The system of claim 7, further comprising an external device, and wherein saving the received thermal image data and/or the generated display image in memory if the thermal image data is considered anomalous comprises uploading the received thermal image data and/or the generated display image to the external device.

9. The system of claim 1, further comprising an auxiliary measurement device configured to measure one or more parameters associated with the target scene, and wherein the statistical thermal profile is associated with the one or more parameters.

10. The system of claim 9, wherein the memory comprises a plurality of statistical thermal profiles and the processor is further configured to:
receive measurement data from the sensor representative of one or more parameters of the target scene; and
select a statistical thermal profile from the memory for comparison with the thermal image data based on the received measurement data.

11. The system of claim 1, wherein the processor is further configured to update the statistical thermal profile with the received thermal image data.

12. The system of claim 1, wherein the thermal camera module is fixed proximate a device under test so that the target scene comprises the device under test and so that acquired thermal image data is representative of approximately the same vantage point of the device under test.

13. The system of claim 1, wherein the IR camera module is housed in a hand-held thermal imaging camera.

14. A thermal analysis system comprising:
an infrared (IR) camera module capable of receiving IR radiation from a target scene and generating corresponding IR image data representative of the heat pattern across the target scene based on the received IR radiation;
a memory in communication with the IR camera module;
an auxiliary measurement device configured to generate measurement data representative of at least one parameter of the target scene
a processor in communication with the auxiliary measurement device, the IR camera module, and the memory, the processor being configured to:
(a) at a plurality of times, capture thermal image data from a target scene using the IR camera module and acquire measurement data from the auxiliary measurement device at approximately the same time as capturing the thermal image data; and
(b) generate a statistical thermal profile of the target scene based on the thermal image data captured at the plurality of times; wherein
the statistical thermal profile comprises, for each of a plurality of regions in the thermal image data, at least two statistical parameters representative of the typical thermal behavior in the target scene in each of the plurality of regions, and
generating the statistical thermal profile comprises associating the captured thermal image data with an operating condition based on the acquired measurement data and generating a statistical thermal profile corresponding to the operating condition.

15. The system of claim 14, wherein the processor is further configured to:
(c) capture further thermal image data from the target scene using the IR camera module;
(d) compare at least a portion of the captured further thermal image data from step (c) to a corresponding portion of the generated statistical thermal profile of the target scene; and
(e) in the event that the portion of the captured further thermal image data is considered sufficiently anomalous with respect to the corresponding portion of the statistical thermal profile of the target scene, perform at least one action.

16. The system of claim 15, further comprising an external device in communication with the processor, and wherein the performing the at least one action comprises alerting a system operator of a detected anomaly via the external device.

17. The system of claim 14, wherein the processor is further configured to:
(c) capture further thermal image data from the target scene using the IR camera module;
(d) acquire measurement data at approximately the same time as capturing further thermal image data from the target scene in step (c) to determine an operating condition of the target scene;
(e) select a statistical thermal profile from memory corresponding to the determined operating condition;
(f) compare at least a portion of the captured further thermal image data from step (c) to a corresponding portion of the selected statistical thermal profile of the target scene; and
(g) in the event that the portion of the captured further thermal image data is considered sufficiently anomalous with respect to the corresponding portion of the selected statistical thermal profile of the target scene, perform at least one action.

18. The system of claim 14, wherein generating the statistical thermal profile comprises determining, for each of a plurality of regions in the captured thermal image data, an average value and a standard deviation.

19. The system of claim 14, further comprising a user interface by which a user can manually exclude captured thermal image data from contributing to the statistical thermal profile.

20. The system of claim 14, wherein the processing steps of (a) capturing thermal image data from a target scene using the IR camera module and (b) generating a statistical thermal profile of the target scene based on the captured thermal image data comprise:
capturing thermal image data;
determining the at least two statistical parameters from the captured thermal image data;
aggregating the determined statistical parameters from the captured thermal image data;
generating the statistical thermal profile using the aggregated statistical parameters; and
discarding the captured thermal image data.

21. A thermal analysis system comprising:
an infrared (IR) camera module capable of receiving IR radiation from a target scene and generating corresponding IR image data representative of the heat pattern across the target scene based on the received IR radiation;
a memory in communication with the IR camera module;
a processor in communication with the IR camera module and the memory, the processor being configured to:
(a) at a plurality of times, capture thermal image data from a target scene using the IR camera module; and
(b) generate a statistical thermal profile of the target scene based on the thermal image data captured at the plurality of times; wherein
the statistical thermal profile comprises, for each of a plurality of regions in the thermal image data, at least two statistical parameters representative of the typical thermal behavior in the target scene in each of the plurality of regions; and
the processing steps of (a) capturing thermal image data from a target scene using the IR camera module and (b)

generating a statistical thermal profile of the target scene based on the captured thermal image data comprise:

capturing thermal image data;

determining the at least two statistical parameters from the captured thermal image data;

aggregating the determined statistical parameters from the captured thermal image data;

generating the statistical thermal profile using the aggregated statistical parameters; and discarding the captured thermal image data.

22. The system of claim 21, wherein the processor is further configured to:

(c) capture further thermal image data from the target scene using the IR camera module;

(d) compare at least a portion of the captured further thermal image data from step (c) to a corresponding portion of the generated statistical thermal profile of the target scene; and (e) in the event that the portion of the captured further thermal image data is considered sufficiently anomalous with respect to the corresponding portion of the statistical thermal profile of the target scene, perform at least one action.

23. The system of claim 22, further comprising an external device in communication with the processor, and wherein the performing the at least one action comprises alerting a system operator of a detected anomaly via the external device.

24. The system of claim 21, further comprising an auxiliary measurement device in communication with the processor and configured to generate measurement data representative of at least one parameter of the target scene; and wherein the processor is further configured to acquire measurement data at approximately the same time as capturing thermal image data from the target scene in step (a); and generating the statistical thermal profile comprises associating the captured thermal image data with an operating condition based on the acquired measurement data and generating a statistical thermal profile corresponding to the operating condition.

25. The system of claim 24, wherein the processor is further configured to:

(c) capture further thermal image data from the target scene using the IR camera module;

(d) acquire measurement data at approximately the same time as capturing further thermal image data from the target scene in step (c) to determine an operating condition of the target scene;

(e) select a statistical thermal profile from memory corresponding to the determined operating condition;

(f) compare at least a portion of the captured further thermal image data from step (c) to a corresponding portion of the selected statistical thermal profile of the target scene; and (g) in the event that the portion of the captured further thermal image data is considered sufficiently anomalous with respect to the corresponding portion of the selected statistical thermal profile of the target scene, perform at least one action.

26. The system of claim 21, wherein generating the statistical thermal profile comprises determining, for each of a plurality of regions in the captured thermal image data, an average value and a standard deviation.

27. The system of claim 21, further comprising a user interface by which a user can manually exclude captured thermal image data from contributing to the statistical thermal profile.

* * * * *